(12) United States Patent
Uber, III et al.

(10) Patent No.: US 9,561,344 B2
(45) Date of Patent: Feb. 7, 2017

(54) FLUID DELIVERY SYSTEMS, DEVICES, AND METHODS FOR DELIVERY OF HAZARDOUS FLUIDS

(71) Applicant: BAYER MEDICAL CARE INC., Indianola, PA (US)

(72) Inventors: Arthur E. Uber, III, Pittsburgh, PA (US); Alan D. Hirschman, Glenshaw, PA (US); David M. Griffiths, Pittsburgh, PA (US); Frederick W. Trombley, III, Gibsonia, PA (US); David M. Reilly, Pittsburgh, PA (US)

(73) Assignee: Bayer HealthCare LLC, Whippany, NJ (US)

( * ) Notice: Subject to any disclaimer, the term of this patent is extended or adjusted under 35 U.S.C. 154(b) by 0 days.

(21) Appl. No.: 14/684,900

(22) Filed: Apr. 13, 2015

(65) Prior Publication Data
US 2015/0231363 A1      Aug. 20, 2015

Related U.S. Application Data

(62) Division of application No. 13/898,680, filed on May 21, 2013, now Pat. No. 9,005,166, which is a division
(Continued)

(51) Int. Cl.
   *A61M 25/00* (2006.01)
(52) U.S. Cl.
   CPC ................. *A61M 25/0045* (2013.01)
(58) Field of Classification Search
   CPC .. A61M 25/0045; A61M 25/00; A61M 29/00; A61M 1/285; A61M 27/00; A61M 31/00; A61M 39/10; A61M 2025/0037; A61M 25/0071; A61M 25/0097
(Continued)

(56) References Cited

U.S. PATENT DOCUMENTS

| | | |
|---|---|---|
| 2,027,588 A | 1/1936 | Hannon |
| 2,112,160 A | 3/1938 | Johnson |

(Continued)

FOREIGN PATENT DOCUMENTS

| | | |
|---|---|---|
| JP | H05264789 A | 10/1993 |
| JP | H06312009 A | 11/1994 |

(Continued)

OTHER PUBLICATIONS

Capitail Pyrimid Glove Box, Guyline Limited website (www.guyline.com.hk).
(Continued)

*Primary Examiner* — Manuel Mendez
(74) *Attorney, Agent, or Firm* — Joseph L. Kent; David Schramm; James R. Stevenson

(57) ABSTRACT

A catheter including an outer conduit and an inner conduit positioned within the outer conduit, the inner conduit having a smaller diameter that that of the outer conduit. A volume between the outer conduit and the inner conduit define a first lumen which may deliver a first fluid to a patient, and an inside diameter of the inner conduit defines a second lumen which may deliver a second fluid to the patient such that the fluid flow of the first fluid and the second fluid exiting the catheter has a flow profile where the first fluid surrounds the second fluid and the second fluid is prevented from contact with inner walls of a blood vessel of the patient in a vicinity of a tip of the catheter.

9 Claims, 14 Drawing Sheets

Related U.S. Application Data of application No. 12/748,682, filed on Mar. 29, 2010, now Pat. No. 8,454,561, which is a division of application No. 10/821,210, filed on Apr. 8, 2004, now Pat. No. 7,713,239.

(60) Provisional application No. 60/461,152, filed on Apr. 8, 2003.

(58) Field of Classification Search
USPC ...... 604/523, 534, 284, 264, 131, 65–67, 82
See application file for complete search history.

(56) References Cited

U.S. PATENT DOCUMENTS

| | | | |
|---|---|---|---|
| 3,191,789 A | | 6/1965 | Davidson |
| 4,092,546 A | | 5/1978 | Larrabee |
| 4,307,713 A | | 12/1981 | Galkin et al. |
| 4,313,440 A | * | 2/1982 | Ashley ............... A61M 5/19 604/191 |
| 4,405,163 A | | 9/1983 | Voges et al. |
| 4,405,312 A | | 9/1983 | Gross et al. |
| 4,409,488 A | | 10/1983 | King |
| 4,467,588 A | | 8/1984 | Carveth |
| 4,512,764 A | | 4/1985 | Wunsch |
| 4,529,401 A | | 7/1985 | Leslie et al. |
| 4,563,175 A | | 1/1986 | LaFond |
| 4,645,073 A | | 2/1987 | Homan |
| 4,747,826 A | | 5/1988 | Sassano |
| 4,853,546 A | | 8/1989 | Abe et al. |
| 4,857,728 A | | 8/1989 | Smith, Jr. |
| 4,874,366 A | * | 10/1989 | Zdeb ............... A61M 5/1409 604/518 |
| 4,925,444 A | | 5/1990 | Orkin et al. |
| 4,936,841 A | | 6/1990 | Aoki et al. |
| 4,966,579 A | | 10/1990 | Polaschegg |
| 5,002,528 A | | 3/1991 | Palestrant |
| 5,039,863 A | | 8/1991 | Matsuno et al. |
| 5,145,083 A | | 9/1992 | Takahashi |
| 5,190,522 A | | 3/1993 | Wojcicki et al. |
| 5,242,403 A | | 9/1993 | Falb et al. |
| 5,244,463 A | * | 9/1993 | Cordner, Jr. ......... A61M 5/142 128/DIG. 12 |
| 5,274,239 A | | 12/1993 | Lane et al. |
| 5,318,517 A | * | 6/1994 | Reiman ............... A61M 1/0084 128/207.14 |
| 5,342,346 A | | 8/1994 | Honda et al. |
| 5,472,403 A | | 12/1995 | Cornacchia et al. |
| 5,492,147 A | | 2/1996 | Challender et al. |
| 5,494,036 A | | 2/1996 | Uber, III et al. |
| 5,562,591 A | | 10/1996 | Marchand et al. |
| 5,569,181 A | | 10/1996 | Heilman et al. |
| 5,739,508 A | | 4/1998 | Uber, III |
| 5,806,519 A | | 9/1998 | Evans, III et al. |
| 5,840,026 A | | 11/1998 | Uber, III et al. |
| 5,843,037 A | | 12/1998 | Uber, III |
| 5,911,252 A | | 6/1999 | Cassel |
| 5,938,636 A | | 8/1999 | Kramer et al. |
| 6,238,374 B1 | | 5/2001 | Winkler |
| 6,258,078 B1 | | 7/2001 | Thilly |
| 6,339,718 B1 | | 1/2002 | Zatezalo et al. |
| 6,397,098 B1 | | 5/2002 | Uber, III et al. |
| 6,440,107 B1 | | 8/2002 | Trombley, III et al. |
| 6,547,787 B1 | | 4/2003 | Altman et al. |
| 6,689,091 B2 | | 2/2004 | Bui et al. |
| 6,767,319 B2 | | 7/2004 | Reilly et al. |
| 7,094,216 B2 | | 8/2006 | Trombley et al. |
| 7,268,359 B2 | | 9/2007 | Fu et al. |
| 7,335,902 B2 | | 2/2008 | Soundararajan |
| 7,712,491 B2 | | 5/2010 | Tochon-Danguy et al. |
| 7,713,231 B2 | | 5/2010 | Wulfman et al. |
| 7,713,235 B2 | | 5/2010 | Torrance et al. |
| 7,713,239 B2 | | 5/2010 | Uber et al. |
| 2003/0004463 A1 | | 1/2003 | Reilly et al. |
| 2003/0036674 A1 | | 2/2003 | Bouton |
| 2003/0036713 A1 | | 2/2003 | Bouton et al. |
| 2003/0216685 A1 | * | 11/2003 | Porter .............. A61B 17/00491 604/82 |
| 2004/0015038 A1 | | 1/2004 | Lemer |
| 2005/0029465 A1 | | 2/2005 | Lemer |
| 2005/0085682 A1 | | 4/2005 | Sasaki et al. |

FOREIGN PATENT DOCUMENTS

| | | |
|---|---|---|
| JP | H06345133 A | 12/1994 |
| JP | H07167754 A | 7/1995 |
| JP | H0811907 A | 1/1996 |
| JP | 2000350783 A | 12/2000 |
| JP | 2002210007 A | 7/2002 |
| JP | 2002306609 A | 10/2002 |
| JP | 2002341040 A | 11/2002 |
| JP | 2003098259 A | 4/2003 |
| WO | 9632887 A1 | 10/1996 |
| WO | 9832411 A1 | 7/1998 |
| WO | 0053242 A1 | 9/2000 |
| WO | 2004091688 A2 | 10/2004 |

OTHER PUBLICATIONS

International Preliminary Report on Patentability for Application No. PCT/US2004/010824, mailed on Oct. 14, 2005, 4 pages.

International Search Report and Written Opinion for Application No. PCT/US2004/010824, mailed on Aug. 29, 2005, 5 pages.

LabVIEW Software, National Instruments website (www.ni.com/labview).

MEDRAD Continuum Infusion System, MEDRAD Inc. website (http://web2.medrad.com/products/mr/continuum.html).

MEDRAD Mark V Injector, MEDRAD Inc. website (http://web2.medrad.com/products/cv/mark-v-provis.html).

MEDRAD Spectris Solaris Injector, MEDRAD Inc. website (http://web2.medrad.com/products/mr/spectris-solaris.html).

MEDRAD Stellant Injector, MEDRAD Inc. website (http://web2.medrad.com/products/ct/stellant.html).

Pegasus Infusion Pump, Instechlabs website (www.instechlabs.com/Pumps/pegasus/index.php).

Pulse Spray Injector, AngioDynamics Incorporated website (www.angiodynamics.com/pages/products/pulsespray.sub.--injector-asp).

* cited by examiner

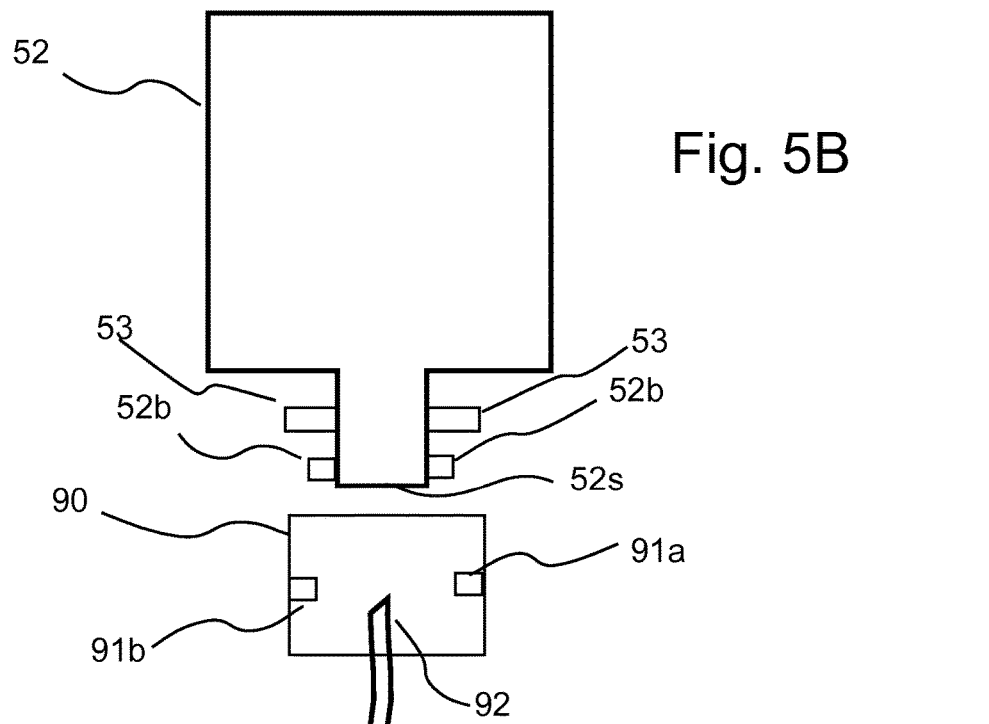
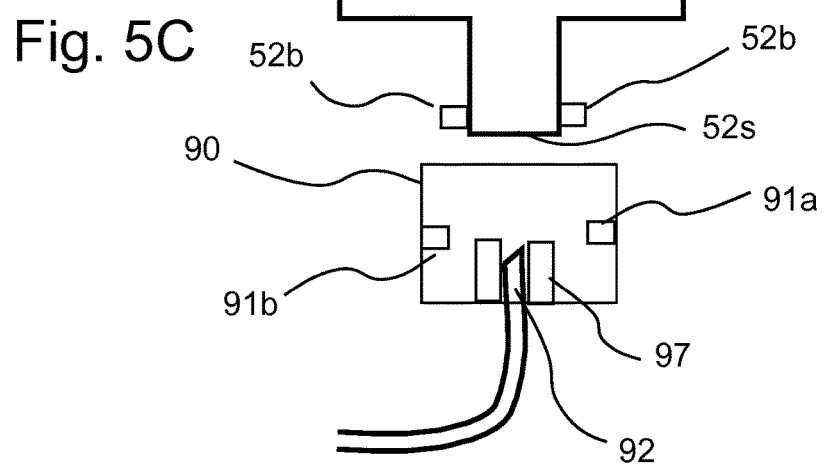
Fig. 5B
Fig. 5C

Fig. 10B
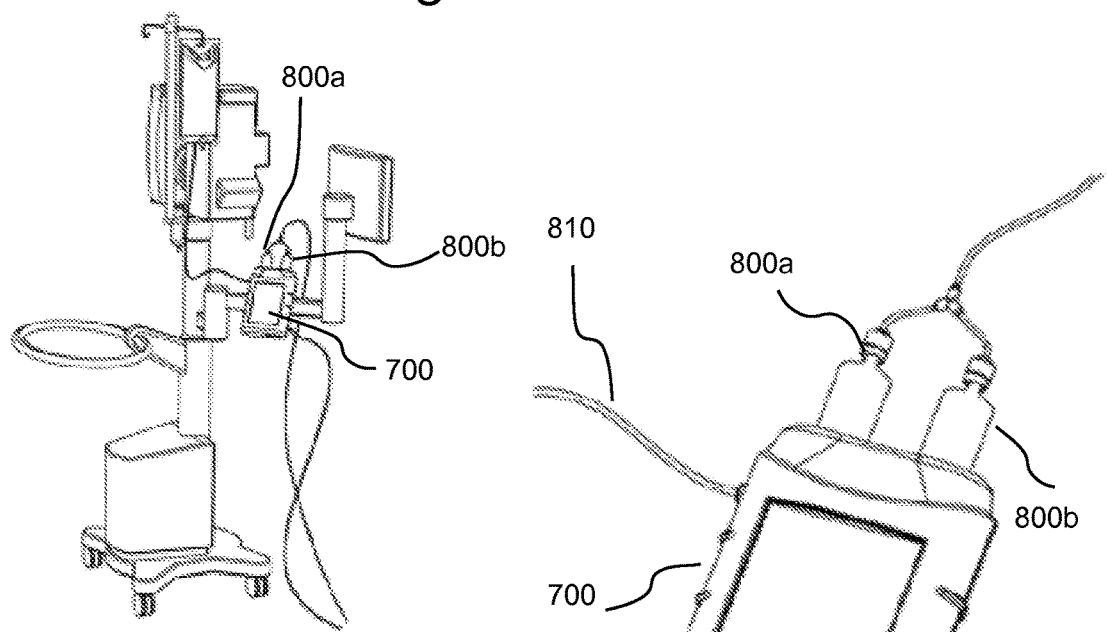
Fig. 10a
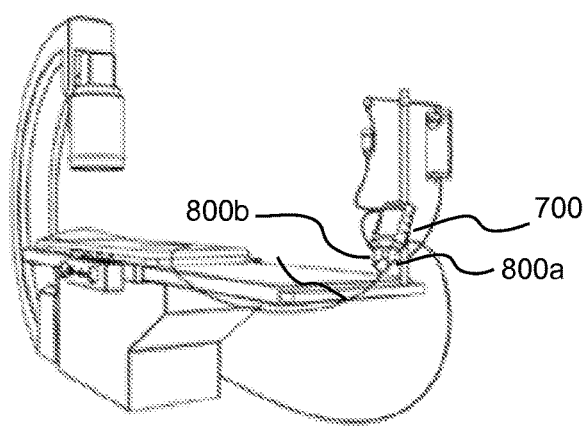
Fig. 10C

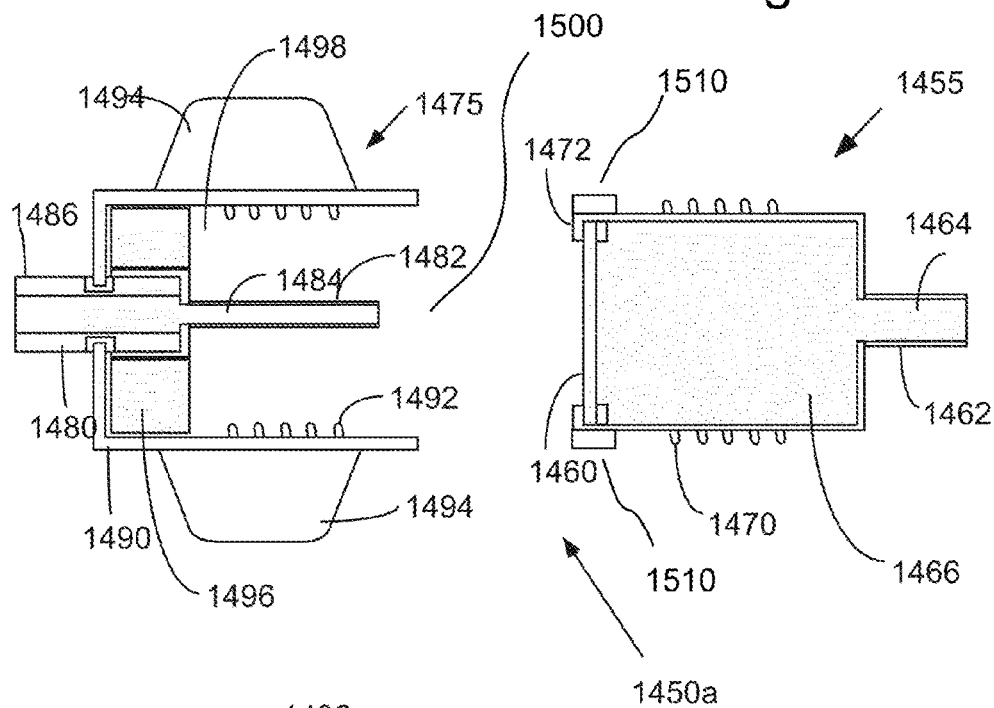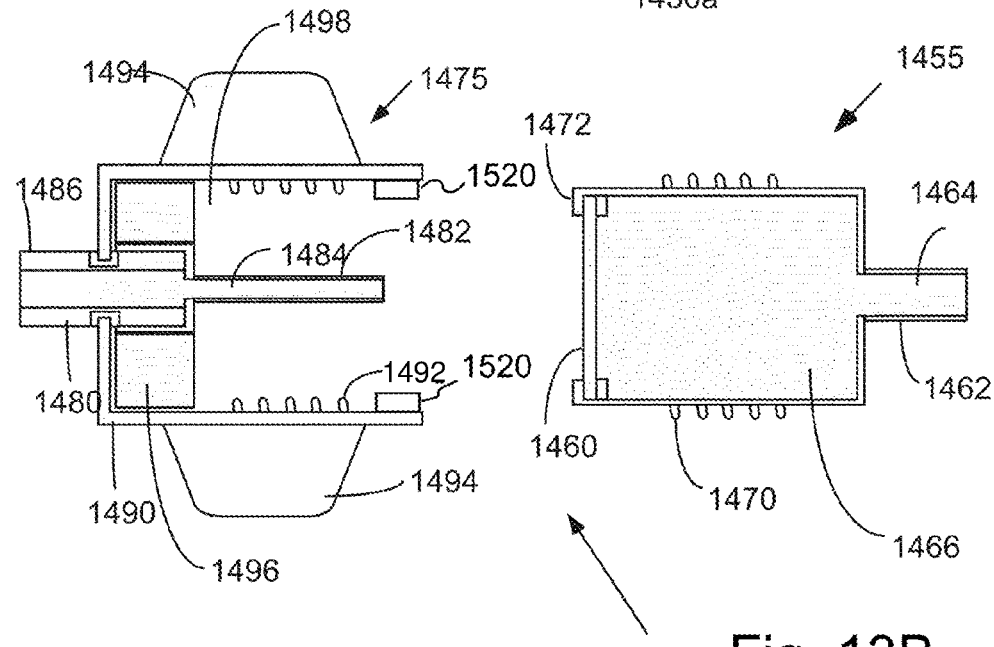

FLUID DELIVERY SYSTEMS, DEVICES, AND METHODS FOR DELIVERY OF HAZARDOUS FLUIDS

CROSS-REFERENCE TO RELATED APPLICATION

This application is a divisional of U.S. patent application Ser. No. 13/898,680 filed May 21, 2013, now U.S. Pat. No. 9,005,166, which is a divisional of U.S. patent application Ser. No. 12/748,682 filed Mar. 29, 2010, now U.S. Pat. No. 8,454,561, which is a divisional of U.S. patent application Ser. No. 10/821,210, filed Apr. 8, 2004, now U.S. Pat. No. 7,713,239, and claims the benefit of U.S. Provisional Patent Application Ser. No. 60/461,152, filed Apr. 8, 2003, the disclosures of which are incorporated herein by reference.

BACKGROUND OF THE INVENTION

The present invention relates generally to fluid delivery systems, to fluid delivery devices and to methods of fluid delivery, and, especially, to fluid delivery systems of hazardous medical fluids, devices for use therein and to methods of delivering hazardous medical fluids to a patient. Current angiographic practice uses X-ray imaging to visualize the inside of the body. Physicians deftly maneuver catheters to a desired blood vessel. X-ray absorbing contrast is injected so that the vessel and downstream vessels can be clearly seen on the X-ray display or film. Using the resultant image, a physician makes a diagnosis and determines appropriate treatment. In interventional procedures, treatment is performed using injection catheters, atherectomy devices, stents, or any one of many interventional devices. Often the interventional treatment is performed during the angiographic procedure, although sometimes treatment is performed at a later time.

During normal angiographic procedures, in addition to contrast it is common to inject saline to flush contrast from the catheter, to keep the catheter lumen open (unclotted), and/or to act as a fluid path for measuring blood pressure. Often the doctor performs the injections by hand, particularly for coronary injections. In some cases, saline is gravity fed.

For peripheral injections, and sometimes for coronary injections, powered injectors are used to inject the contrast because of its high viscosity and the high pressures required to drive contrast through small catheter diameters. Powered injectors can, for example, develop pressures up to 1200 psi in such injections. The pressure range used in such injections is well above the pressure a person can practically develop via hand injection. U.S. Pat. Nos. 5,494,036, 6,339,718, 5,843,037, 5,840,026, 5,806,519, 5,739,508, and 5,569,181, assigned to the assignee of the present invention, which are incorporated herein by reference, disclose the use of powered injector systems that are capable of injecting contrast, saline, and other fluids, either at the same time or in sequence.

In thrombolytic therapy, a doctor places a catheter to study a blockage of a vessel. The doctor then uses a plain catheter or one of many special thrombolytic catheters to inject a thrombolytic agent into the clot. Sometimes the injection is performed using periodically pulsed high-pressure injections to drive the thrombolytic agent into the clot and speed its breakdown. Examples of injectors suitable for use in thrombolytic procedures include the Pulse*Spray Injector Model PSI-1 available from AngioDynamics of Queensbury, N.Y. and the Pulse Thrombolytic Pump PTP1 available from Linet Compact s.r.o. of the Czech Republic.

A difficulty with such currently available injection devices is the requirement that the doctor manipulate the fluid path, sometimes having to disconnect the manual contrast injection syringe and connect the thrombolytic injector. This manipulation takes time, and carries some risk of operator error, including inadvertent biological contamination.

Another interventional procedure under development involves the injection of gene therapies. The goal of one type of gene therapy is to cause the heart muscle to express a gene that causes growth of new blood vessels to nourish heart muscle in which supply arteries have become significantly narrowed by disease. In one type of such gene therapy, the gene therapy DNA is contained in a non-replicating virus. When injected into the body, this virus transfects cells with the contained DNA. As the virus does not contain the DNA required for replicating the virus, it does not multiply and cause disease. These viruses can transfect any cells that they contact with the gene therapy DNA. For this reason, it is important to ensure that the vector viruses are delivered to target tissues only, and to make sure that the hospital personnel are sufficiently protected from contact with the vector virus.

Another application of gene therapy is to block angiogenesis as a way to reduce tumor growth. In this application it is also important that the gene therapy be delivered to the target tissue and that delivery to healthy tissue and health care workers be minimized There are also many other gene therapy applications under study, for example treating cystic fibrosis and muscular dystrophy.

In a representative procedure using an adenovirus gene therapy product, practitioners perform the following steps: (1) storing frozen vials in the pharmacy; (2) in a pharmacy hood, using gloves and proper technique, thawing the bottle with the gene therapy drug in the hand, avoiding agitation; (3) using a needle, pulling a few ml of drug into a hand syringe, for example a 10 ml syringe; (4) adding a few ml of saline to dilute the drug; (5) placing the hand syringe in a syringe holder for transport to the interventional suite to preserve the sterility of the outside of the syringe (the thawed drug has to be used within several hours); (6) for use in the interventional suite, donning goggles and masks (doctors, nurses, technicians) with M-95 filters to protect against infection from airborne viruses; (7) purging the fluid lines of air; (8) diluting the drug further if needed; (9) positioning the catheter in the desired vessel using normal angiographic equipment (manifolds, catheters, guidewires) and technique (normally this is a deep subselective placement to avoid any reflux of contrast or drug into the aorta, where it would be distributed systemically); (10) verifying the placement of the catheter with a contrast injection; (11) optionally flushing the manifold and/or catheter with saline by removing the contrast syringe and attaching the saline syringe; (12) disconnecting the saline syringe; (13) connecting the gene therapy syringe; (14) injecting by hand approximately 1 to 5 milliliters of the gene therapy drug over 1 to 2 minutes; (15) disconnecting the gene therapy syringe; (16) connecting the saline syringe; (17) injecting a few ml of saline over the same time period (e.g., 1 to 2 minutes) to flush the gene therapy drug out of the fluid path and into the patient; (18) disconnecting the saline syringe; (19) reconnecting the contrast syringe; (20) injecting contrast to confirm that the catheter has not moved; (21) repositioning the catheter for the next injection; (22) repeating prior steps until all vessels are injected; and (23) disposing of the disposable parts of the systems (as biohazardous material).

There are a number of drawbacks or unmet needs with the current systems and processes for gene therapy delivery. For example, an enclosed preparation hood is required.

Furthermore, disconnecting and reconnecting multiple syringes for delivering contrast, saline, and drugs is time consuming and increases the risk that some of the drug may be spilled or aerosolized and thus infect the operator and/or the patient in an undesired fashion, or that the drug may be contaminated.

Moreover, it is very difficult for a human to inject a fluid at a steady rate, especially for slow rates (ml/min) extending more than a minute. Motion at a slow rate suffers from stick-slip friction in the syringe, and it takes significant concentration to do it for two 1-2 minute periods up to five times in a procedure. There is significant risk of accidental jerking or bolus injection that either wastes drug or causes it to reflux into the aorta and travel elsewhere in the body. Also, as syringes are connected and disconnected, the plunger can be unintentionally bumped and a bolus of drug injected into the patient or expelled into the environment. Additionally, the changeover time from drug syringe to saline syringe causes an uncontrolled break in therapy injection. As the drug is susceptible to clump formation if agitated, manually connecting and disconnecting the syringe provides opportunities for agitation and clumping.

As mentioned, deep sub-selective catheter placement is needed to avoid drug reflux into the aorta. However, such catheter placement introduces the risk of reducing blood flow through that artery and increases the possibly of causing dissections. Moreover, deep sub-selective catheter placement is more difficult technically to achieve.

Multiple manual manipulations of syringes and the manifold connected to the catheter in the patient increases the risk that the catheter position will be accidentally shifted from optimum placement.

Multiple manual manipulations also increases the risk of errors, such as injecting saline first, and then the drug, and thus having the drug in the catheter being injected into the aorta when it is being moved from one vessel to another.

All procedures that provide access to a patient's blood vessels require that a sterile field be created and maintained to protect the patient against infections. Operators with sterile gloves cannot touch anything that is not sterile, and operators with non-sterile gloves cannot touch anything that goes into the sterile field. In addition, anything that touches the patient, and especially anything that touches bodily fluids, such as blood, has to be disposed of as a biohazardous material. And, as mentioned above, the gene therapy drug itself, even when uncontaminated, poses a biohazard.

Similarly, aerosolization or spillage of chemotherapy agents during preparation or delivery can create hazardous conditions for health care workers or nearby people. Preparation of chemotherapy agents is generally done in a pharmacy in a hood, to protect the pharmacy workers. Chemotherapy agents can be administered intra-arterially into the vessels supplying nourishment to tumors. This has the benefit of giving the tumor a very high dose while keeping the total systemic dose (and thus tissue damage and side effects) to a minimum. It has the downside of requiring the occupation of the expensive facilities of a catheterization or special procedures suite. More commonly, chemotherapy drugs are administered through peripheral intravenous catheters, PICC lines, central venous catheters, or infusion ports. The drug is injected with a hand syringe or an infusion pump, often into a side port of an infusion line connected to one of the venous access devices mentioned above. It is commonly done in the patient's room, an outpatient clinic, or more recently in the patient's home. The making and breaking of connections provides the opportunity for drug spillage or aerosolization and thus transmission to nearby personnel. In chemotherapy administration masks and goggles are not routinely used.

With intra-arterial administration of chemotherapy, the tumor receives the drug directly. With intra-venous administration, many chemotherapy agents damage the veins in which they are injected. This causes local reactions and pain, and it makes it difficult for health care workers to subsequently be able to insert a catheter into the vein.

A third situation which can involve the delivery to a patient of potentially hazardous drugs with associated concern about exposure of other personnel are intramuscular and subcutaneous injections. There are many clinical trials and much research being focused on intramuscular injection of gene therapies and biologics. The needle of a hand syringe is inserted through the skin into the target muscle. Then a controlled amount of drug is injected. Each time the needle is removed from one site and moved to another there is the opportunity for aerosolization and/or spillage since the drug is present at the needle tip.

While it is not yet widely done for gene therapies, inhalation of drugs is a common practice for asthma drugs, is being studied for other drugs, and is another application in which nearby personnel can inadvertently be contaminated by the drug being administered to a patient. As more potent drugs are administered this way, the effects of accidental exposure will become more prevalent. In this case, the drug is intentionally delivered as an aerosol of a liquid or a power, so the problem is particularly severe. All of the aerosol that is put into the air conduits and the patient's airways is not deposited in the patient's body. Thus there is a significant amount of aerosol that could be accidentally released.

It is desirable to develop systems, devices and methods of delivering or administering hazardous pharmaceuticals to patient that reduce and/or eliminate one or more of the problems with current systems, devices and methods described above as well as other problems.

SUMMARY OF THE INVENTION

In one aspect, the present invention provides a system for injecting a patient including a container enclosing a hazardous pharmaceutical; a first pump to deliver a hazardous pharmaceutical to the patient and a fluid path operably connected to the first pump, the container, and the patient. The system further includes a hazardous material containment suitable to confine the hazardous pharmaceutical during connection of the hazardous pharmaceutical container to the fluid path.

The hazardous materials containment can, for example, include a sealable opening adapted to enable placement of the container in the hazardous materials containment prior to connecting the container to the fluid path. The hazardous materials containment can also include a connector in fluid connection with a conduit passing through the hazardous materials containment in a sealed manner. In that embodiment, the connector is adapted to make a fluid connection with the container. The conduit is adapted to be connected to the fluid path.

The system can include at least a second pump operably connected to the fluid path to deliver at least one nonhazardous fluid to the patient. The nonhazardous fluid can, for example, be a fluid suitable to flush the medication out of the fluid path and into the body or a fluid suitable to dilute the hazardous pharmaceutical. The nonhazardous fluid can, for example, be saline. The system can further include a third pump operably connected to the fluid path, which is in fluid connection with a source of a third fluid (for example, a contrast fluid).

The system can also include a waste container in fluid connection with the fluid path. Preferably, the waste container is suitable to contain a hazardous pharmaceutical.

The system can further include at least one valve to control flow through the fluid path. The system can also include a controller to control the operation of at least the first pump and the second pump. A user interface can be in operative connection with the controller.

In one embodiment, the hazardous material containment includes a temperature regulator to control the temperature of the hazardous material container.

The hazardous material containment can include a flexible barrier to surround the hazardous pharmaceutical container. The hazardous material containment can also include a container having a removable lid to enable placement of the hazardous pharmaceutical container within the hazardous material containment. In this embodiment, the hazardous material containment further includes a sealing bather through which a fluid path element can pass to be placed in fluid connection with the hazardous pharmaceutical container. The sealing barrier is suitable to prevent passage of the hazardous pharmaceutical to the environment outside of the hazardous material containment. The hazardous material containment can also include at least one sealing member which forms a seal with the hazardous pharmaceutical container.

The first pump and other pump(s) of the system can be included in a single injector. In one embodiment, each of the pumps is energized. The term "energized" or "apparatus energized" refers to the application of energy (for example, mechanical energy or thermal energy), other than by direct manual manipulation. Typically, electrical energy or stored mechanical energy is used in energizing the devices of the present invention.

The system can further include a measurement apparatus that detects a physiological signal of the patient and a controller that controls fluid delivery from at least one of the first pump and the second pump based upon the physiological signal to control (for example, synchronize) fluid delivery in relation to an organ function.

In one embodiment of the system of the present invention, the container is a vessel in which the hazardous pharmaceutical is distributed by a manufacturer. The container can enclose sufficient hazardous pharmaceutical for delivery to multiple patients. In another embodiment, the container is filled with the hazardous pharmaceutical using a loading device that maintains biohazardous materials containment. Once again, the filled container can enclose sufficient hazardous pharmaceutical for delivery to multiple patients.

The fluid path of the system can include a catheter which is adapted to terminate in a blood vessel of the patient. In one embodiment, the catheter includes two lumens arranged such that flow from the outer lumen substantially surrounds flow from the inner lumen. A catheter can be connected to the fluid path of the system by a connector that provides biohazard containment during connection.

In one embodiment of the system of the present invention the fluid path comprises at least two fluid path elements that are connected by at least one connector that provides biohazard containment during connection.

In an embodiment of the system of the present invention including a controller, the controller can change flow rate over time. For example, the controller can changes the flow such that there are periods of time during which flow rate is increased.

In another aspect, the present invention provides an assembly for connection to an injector. The injector includes a retention mechanism to retain the assembly and a pressurizing mechanism to pressurize one or more fluids within the assembly for delivery to a patient. The assembly includes at least a first compartment defining an enclosure adapted to enclose a hazardous pharmaceutical container enclosing a hazardous pharmaceutical. The first compartment is adapted to prevent hazardous materials from escaping from the first compartment into the surrounding environment. The first compartment includes a first connector to establish a fluid connection with the hazardous pharmaceutical vessel and at least a first outlet in fluid connection with the first connector. The assembly can further include at least a second compartment adapted to contain a fluid other than the hazardous pharmaceutical, the second compartment being in fluid connection with the first outlet.

In another aspect, the present invention provides a system for injecting a pharmaceutical into a local circulation associated with an organ of a patient. The system includes a first pump for injecting the biohazardous pharmaceutical into the local circulation; a fluid path operably connected to the first pump and disposed between the first pump and the patient; a second pump operably connected to the fluid path for injecting a fluid sufficient to flush the pharmaceutical out of the fluid path and into the patient; a measurement apparatus that detects a physiological signal of the patient; and a controller that controls fluid delivery from at least one of the first pump and the second pump based upon the physiological signal to control (for example, synchronize) fluid delivery in relation to an organ function. In one embodiment, the physiological signal is related to heart phase. The synchronization relative to heart phase can, for example, prevent reflux of the pharmaceutical from a local circulation into a system circulation of the patient. In another embodiment, the physiological signal is related to respiration phase.

In a further aspect, the present invention provides a system for injecting a patient, including: a first pump for delivering a hazardous pharmaceutical to a patient and a fluid path operably connected to the first pump and disposed between the first pump and the patient. The first fluid path includes at least one fluid path element. The system further includes a second pump operably connected to the fluid path for injecting a fluid sufficient to flush the hazardous pharmaceutical out of the fluid path and into the patient. The system also includes a hazardous material containment to confine hazardous materials during at least one of establishment, modification, and disposal of fluid path elements.

In another aspect, the present invention provides a method of administering a hazardous pharmaceutical to a patient, including: operably connecting a container in which the hazardous pharmaceutical is distributed to a fluid path in operative connection with a pump. The pump is adapted to administer the hazardous pharmaceutical to the patient. The method can further include placing the container in a hazardous materials containment suitable to confine the hazardous pharmaceutical prior to and during connection of the container to the fluid path. The hazardous materials containment can include a sealing septum through which connection with the container is made.

In another aspect, the present invention provides a catheter including an outer conduit, and an inner conduit positioned within the outer conduit and having a diameter smaller than the outer conduit. The volume between the outer conduit and the inner conduit defines a first lumen adapted to deliver fluid to the patient. The inside diameter of the inner conduit defines a second lumen adapted to deliver a fluid to the patient. In one embodiment, the inner conduit ends rearward of the outer conduit. The flow from the inner conduit can be substantially circumferentially surrounded by the flow from the outer conduct.

In a further aspect, the present invention provides a container including a flexible sealing member that cooperates with a connector to create a biohazard seal during connection of the container to the connector. The flexible sealing member can, for example, be circumferential. The flexible sealing member can also be axially compressed during connection.

In another aspect, the present invention provides a connector including a first member and a second member. At least one of the first member or the second member includes a biohazard seal adapted to contain biohazardous material during connection of the first member and the second member.

In another aspect, the present invention provides a container for a biohazardous material including a first septum sealing a port into the container and a second septum sealing the port. The second septum is spaced from the first septum.

In an another aspect, the present invention provides a system for transferring a pharmaceutical, including: a first container enclosing a hazardous pharmaceutical; a second container to receive the hazardous pharmaceutical; a first pump to deliver a hazardous pharmaceutical from the first container to the second container; a fluid path operably connected to the first pump, the first container, and the second container; and a hazardous material containment suitable to confine the hazardous pharmaceutical during connection of the first container to the fluid path.

In a further aspect, the present invention provides a syringe loading device including at least a first compartment adapted to removably receive a first syringe. The first syringe includes a plunger slidably disposed therein. The first compartment includes a syringe connector adapted to make a fluid connection with the first syringe. The syringe loading device further includes a first container dock adapted to form a sealed engagement with a first fluid container which contains a hazardous pharmaceutical. The first container dock includes a first container connector adapted to make a fluid connection with the first container. The first container connector is in fluid connection with the syringe connector. The syringe loading device further includes an actuator adapted to apply force to the first syringe plunger to draw fluid from the first container into the first syringe. The syringe loading device of can further include at least a second container dock adapted to form an engagement with a second fluid container. The second container dock includes a second container connector adapted to make a fluid connection with the second container. The second container connector is in fluid connection with the syringe connector. The syringe loading can further include a switch to control whether the fluid is drawn into the syringe from the first container or the second container.

In still a further aspect, the present invention provides an injector including a first compartment adapted to receive a first syringe. The first syringe has a hazardous pharmaceutical within a barrel thereof and includes a plunger slidably disposed within the syringe. The injector further includes a first plunger drive in operative connection with the first compartment; an energy storage mechanism adapted to store mechanical energy applied manually to the first plunger drive and a second compartment adapted to receive a second syringe. The second syringe also includes a plunger slidably disposed within the syringe. The injector further includes a second plunger drive in operative connection with the second compartment; an energy storage mechanism adapted to store mechanical energy applied manually to the second plunger drive; and at least one control to regulate the application of stored mechanical energy to the plunger of the first syringe and to the plunger of the second syringe.

The present invention provides a number of improvements over current methods for delivery of hazardous pharmaceutical to patients, For example, the present invention provides enclosures sufficient to protect the operator and patient during preparation and loading of the drug. Certain embodiments of the present invention incorporate an integrated fluid path, preferably a closed path, for both sterility and the safety for operators. The present invention likewise provides energized pumps or regulators to provide consistent, steady flow rates over time frames not practical for humans.

The systems of the present invention can, for example, incorporate diagnostic information (flow rate to reflux) to set therapeutic parameters. An integrated multi-fluid controller/sequencer can also be incorporated in the systems of the present invention to make procedures easier for the operator, and more consistent and safer for the patient. The present invention can also provide a record of the fluid administration parameters.

The systems, devices and methods of the present invention can be used with X-ray, MR, CT, ultrasound or other medical imaging modalities, and can beneficially inject many fluids and types of fluids in addition to gene therapy drugs.

BRIEF DESCRIPTION OF THE DRAWINGS

Other aspects of the invention and their advantages will be discerned from the following detailed description when read in connection with the accompanying drawings, in which:

FIGS. 5A, 5B, and 5C illustrate other embodiments of a biohazard containment for a biohazardous pharmaceutical container.

FIG. 10A illustrates a perspective view of an embodiment of a powered injector or pump of the present invention for use with two front-loading syringes.

FIG. 10B illustrates the pump of FIG. 10A supported on the arm of a mobile support system in association with an angiographic injector.

FIG. 10C illustrates the pump of FIG. 10A attached to a support extending from the patient table of an imaging system.

FIGS. 13a, 13b, 13c and 13d illustrate several embodiments of connectors for joining two fluid path segments.

DETAILED DESCRIPTION OF THE INVENTION

Figure 1:
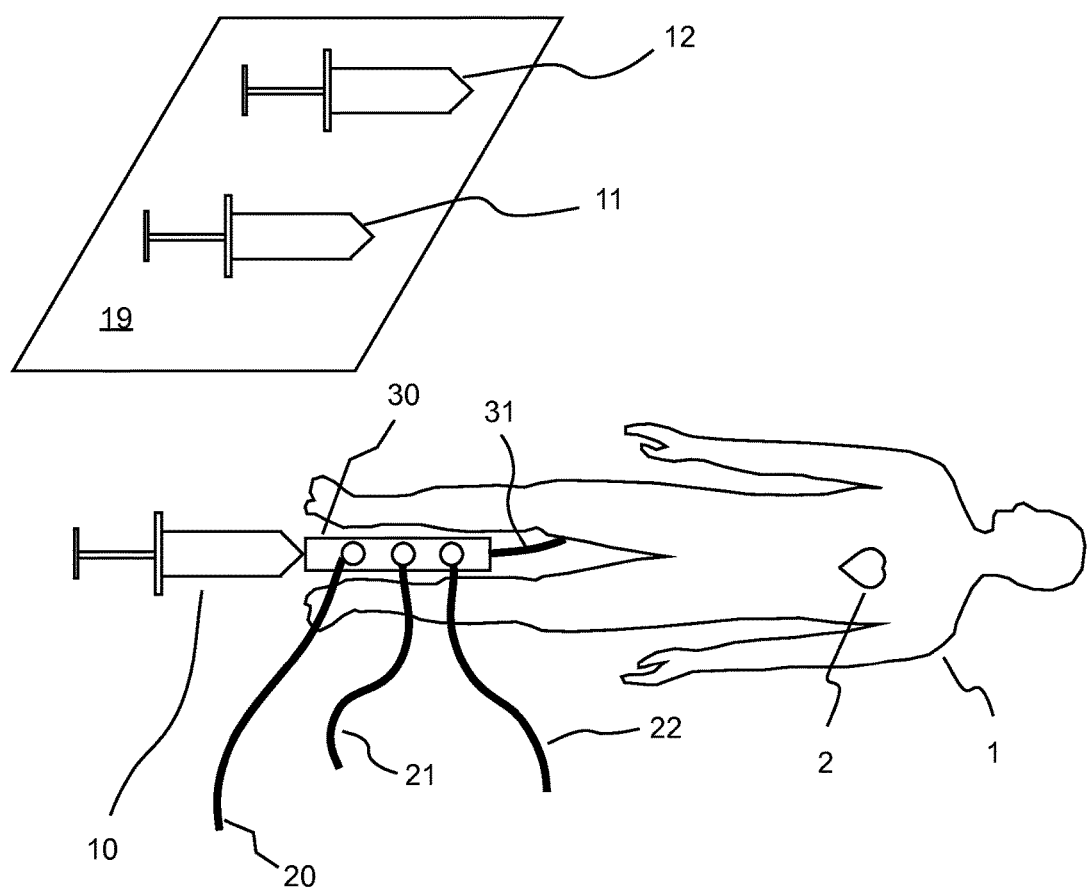
FIG. 1 illustrates an example of a fluid delivery system currently used in gene therapy.

A system currently used for the injection of a gene therapy drug is illustrated in FIG. 1. In FIG. 1, a patient 1 has a catheter 31 inserted via a femoral (leg) artery into the arteries nourishing the patient's heart 2. A number of catheters with single or dual side-by-side lumens are commonly used. The catheters can have just an end hole, or multiple side holes to increase the mixing of the drug with the blood. An infusion catheter slid inside a guiding catheter is also commonly used. Other arteries can be used for accesses as well. The external end of a catheter 31 is connected via a connector to a manifold 30, either directly or with an intermediate piece of tubing (not shown). Other common angiographic equipment and personnel such as a guide wire, a hemostasis valve, an X-ray imaging system, an MR imaging system, an ultrasound imaging system, or other imaging equipment, as well as physicians and nurses are not shown in FIG. 1.

Manifold 30 has several valves, typically three or four, which in the system of FIG. 1 connect to three lines. Line 22 is connected to a blood pressure measuring device (not shown), line 21 is connected to a saline bag, bottle, container, or reservoir (not shown), and line 20 is connected to a contrast bag, bottle, container, or reservoir (not shown). A hand-operated syringe 10 is used to inject contrast or saline, depending upon whether it is filled from line 20 or from line 21. The region surrounding the vascular access site and nearby areas of the patient are covered by sterile cloths and the exposed skin near the vascular entry point is sterilized. There is typically an adjacent work surface or cart that has a flat sterile surface 19 to hold sterile instruments and supplies ready for use. For the situation in which a gene therapy drug is to be injected, syringe 12 contains the gene therapy drug and syringe 11 contains the saline used to follow the gene therapy injection and flush the gene therapy drug from the fluid path and into the patient. As described above, the doctor manually connects, fills, injects, and disconnects syringes 10, 11, and 12 to achieve the desired sequence of fluid delivery. And each time a connection is made, the doctor has to ensure that bubbles are not created that can be injected into the patient and cause strokes or damage to other organs.

Figure 2:
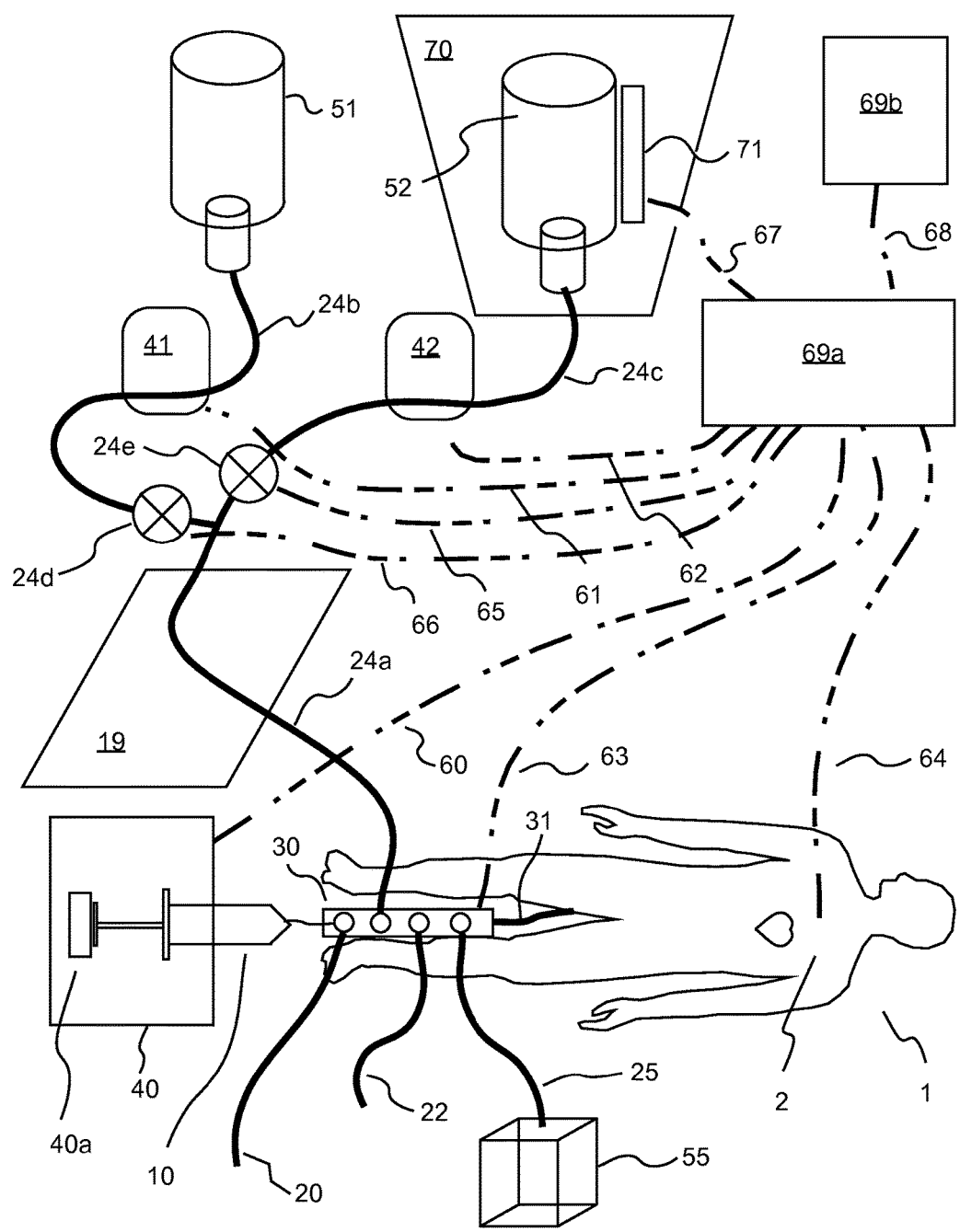
FIG. 2 illustrates one embodiment of a fluid delivery system of the present invention.

FIG. 2 illustrates one embodiment of a fluid delivery system of the present invention. In the embodiment of FIG. 2, patient 1 has a catheter 31 inserted via a femoral approach into the patient's heart 2. Catheter 31 is connected to a manifold 30 to enable injection of various fluids. Syringe 10 can be filled with contrast from line 20 and then injected. In this embodiment, syringe 10 is operated by a mechanical injector 40 including a piston 40a that pushes or pulls on the syringe plunger extension, thereby moving fluid in and out of syringe 10. An injector or syringe pump, such as the ProVis® angiographic injector available from Medrad, Inc. of Indianola, Pa., can, for example, be used as pump 40.

Pump 42 delivers the gene therapy drug or other drug. In this embodiment, the drug remains in its container 52 and is pumped from the container by a peristaltic pump 42. The drug flows through tubing 24c and then tubing 24a into the manifold and thence into patient 1. Tubing 24c and 24a can, for example, be microbore tubing to minimize the amount of fluid or dead space in the tubing itself. In the embodiment of FIG. 2, pump 42 and the drug containing apparatus are outside the sterile field. The fluid is brought into the sterile field through sterile tubing 24a. Drug container 52 can be any container which preserves the sterility and utility of the drug including, for example glass bottles, bags, carpules, or prefilled syringes. If container 52 (or any other fluid container in the system) is rigid, a vacuum will be created as fluid is pulled out. There are several methods to eliminate this problem. For example, air can be injected into the container before removal of the fluid, or the needle or spike used to remove the fluid can be vented with a hydrophobic filter or with a one way valve and filter that allows sterile air to enter the container as the fluid is removed but prevents any leakage of the fluid.

A biohazard containment or enclosure 70 enables spiking and withdrawal of the gene therapy drug from drug container 52 outside of the pharmacy and, indeed, outside of a hood. One end of fluid path element 24c penetrates and is sealed to biohazard enclosure 70. The spike, needle, or other mechanism for making fluid connection to drug container 52 is inside biohazard enclosure 70 and is sheathed to protect the operator and enclosure 70. During use, biohazard enclosure 70 is opened, and drug container 52 is placed inside. Then, biohazard enclosure 70 is sealed and container 52 is connected to fluid path 24c using gloves or other flexible handling devices that operate through the walls of biohazard enclosure 70. If biohazard enclosure 70 is flexible, it does not need to be vented. If it is rigid or semi-rigid, it preferably incorporates a vent, which is preferably adapted or designed to contain any aerosolized biohazardous material. The vent can incorporate activated charcoal or a zeolite material if it is necessary or desired to contain drug vapors as well. The in-suite biohazard enclosure 70 of the present invention saves considerable time, labor and expense by eliminating the syringe filling steps in the pharmacy. Biohazard enclosure 70 can for example, include a Captair Field Pyramid glove box available from CAPTAIR™ LABX, INC. of North Andover, Mass.

Figure 4:
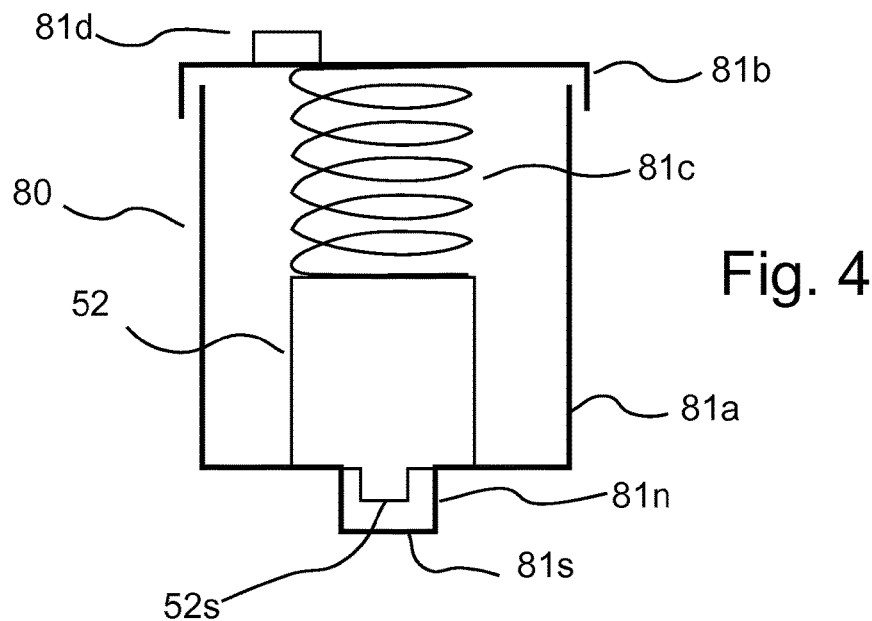
FIG. 4 illustrates another embodiment of a biohazard container of the present invention for use with a biohazardous drug or pharmaceutical bottle.

Another embodiment of a biohazard enclosure 80 of the present invention is shown in FIG. 4. Biohazard enclosure 80 includes a vessel 81a having a neck 81n that is, for example, formed, adapted or designed so that the outside of the neck or lid of drug container 52 fits tightly into the inside of enclosure neck 81*n*. Drug container 52 is, for example, held against the bottom of enclosure 80 by a biasing member such as spring 81*c* when lid 81*b* is installed onto vessel 81*a*. Lid 81*b* can, for example, be retained by threads or by other means. Preferably, a seal is formed between lid 81*b* and vessel 81*a* which is sufficient to prevent egress of any biohazard material. The seal can, for example, be molded into either or both of lid 81*b* and vessel 81*a*. Alternatively, the seal can be a separate elastomeric seal. In the embodiment of FIG. 4, biohazard enclosure 80 includes an optional filtered vent 81*d* to allow air movement to equilibrate pressure between the inside and the outside. During use, the needle or spike connected to the distal end (farthest from patient) of tubing 24*c* first pierces enclosure septum 81*s*. It then is pushed farther and pierces drug container septum 52*s*. Any leakage of biohazardous drug is contained within enclosure 80. If the enclosure is designed to fit one size of bottle, then spring 81*c* can be functionally included into lid 81*b* by, for example, simply bulging lid 81*b* inward enough that it holds drug container 52 in place. Vessel 81*a* and lid 81*b* can, for example, be manufactured by vacuum forming or by injection molding. Alternatively, vessel 81*a* can be flexible with a seal such as found in a ZIPLOC® bag. In this case, vessel 81*a* can have a rigid or elastomeric segment that mates with the neck of the drug container.

It may be advantageous if the drug bottle is distributed with an integral biohazard enclosure such as illustrated in FIG. 4. The drug bottle can, for example, either come with the biohazard enclosure in place, or with the biohazard enclosure in the same package, to be installed as soon as the package is opened. A biohazard containment mechanism can be achieved by incorporating the double septum feature (81*s* and 52*s*) onto neck of the container.

An alternative embodiment that provides some indication of the efficacy or patency of the sealed enclosure can be formed by connecting filtered vent 81*d* to a low flow rate vacuum pump, either continuous or periodically operating, either manual or automatic. By measuring the pressure in the enclosure, any compromise of the enclosure, will be indicated by a pressure rise and an alarm or indication can be made to the operator.

Figure 5A:
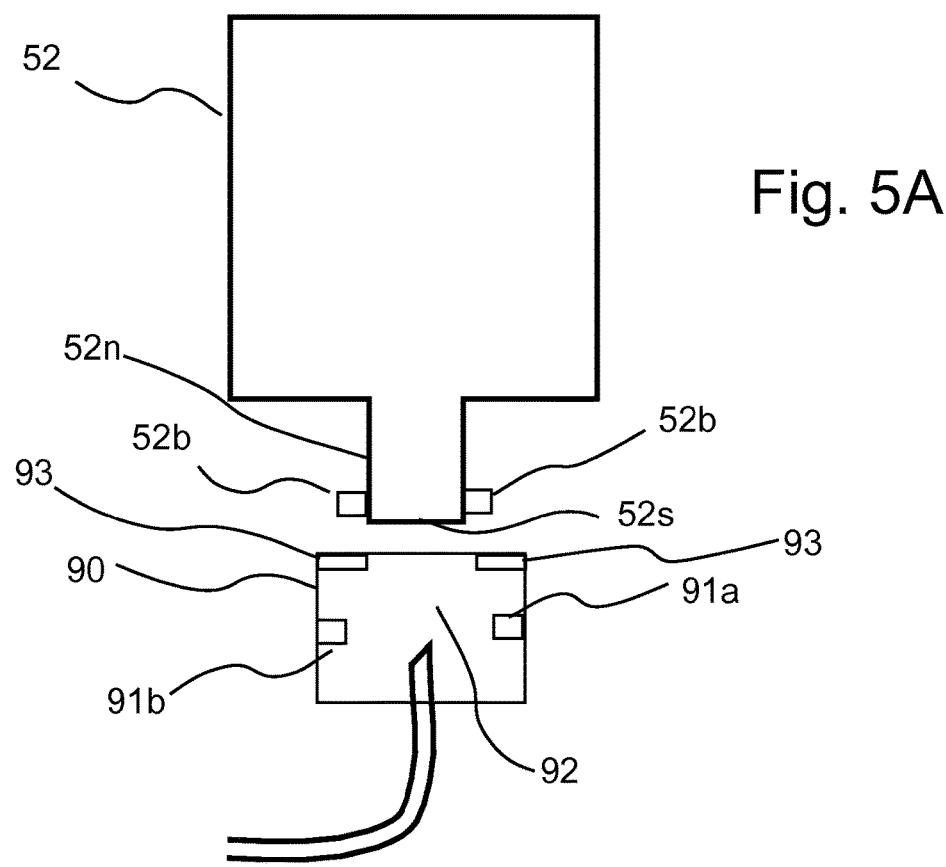

Another embodiment of a biohazard enclosure is illustrated in FIG. 5A. In the embodiment of FIG. 5A, rather than wholly enclosing drug container 52, needle 92 that pierces drug container septum 52*s* is preconnected to fluid path 24*c* and is part of an "on only" cap 90 that is pushed on once and then cannot be removed from container 52 (except with considerable force and/or effort). Bumps 91*a* and 91*b* can, for example, elastically deform as cap 90 is pushed on. Bumps 91*a* and 91*b* engage lip 52*b* of the container 52 and prevent the removal of cap 90. Flexible sealing member 93 flexes to allow lip 52*b* to pass, and then seals against the neck 52*n* of the container 52. The air inside cap 90 is vented through vent 94. The sealing member 93 can be permanently attached to the cap 90, or be press fit, or be installed into the cap before use by the user. FIG. 5B shows the sealing member 53 mounted on the fluid container. It could come mounted or come demounted and be mounted by the user before mating with the cap 90. FIG. 5C shows a third embodiment, wherein the seal is between a deformable member 97 and the front of the container neck or optionally with the front of lip 52*b*. In this embodiment, the seal is made to deformable member 97 before the needle 92 pierces the septum 52*s*. Additional motion of the cap 90 towards the container 52 maintains the seal, pierces the septum 52*s* and establishes the fluid path. The deformable member 97 or seals 93 or 53 can be for example, a bellows, a thin deformable structure, a sufficiently soft elastomer, a gel, a closed cell foam, or an open cell foam with pores or surface finish sufficient to prevent egress of any hazardous materials. If an open cell foam is used, it can incorporate the air venting function such that a separate vent is not needed. The sealing options discussed subsequently in relation to biohazard containment connectors can also apply here. Alternatively, container 52 and cap 90 can be provided with cooperating threading for forming a sealed connection therebetween. By connecting fluid path 24*c* to the other fluid path elements before connection to drug container 52, the biohazard containment of the drug or pharmaceutical is completed without full physical enclosure of container 52. While FIGS. 5A, 5B, and 5C are illustrated with a needle piercing a septum, it could also use a needleless connector such as the InterLink® system, a make only luer connection, or any other suitable fluid connection.

By eliminating or preventing the opening of the liquid connection, a significant source of aerosol generation is removed by the system of FIG. 5.

An alternative to a tightly sealed enclosure is a less tightly sealed, passive enclosure that includes germicidal, viruscidal, or chemical destroying agents, devices or substances. Examples of germicidal, viruscidal, or chemical destroying agents, devices or substances include, but are not limited to, ultraviolet light, hydrogen peroxide vapor, activated charcoal, and ozone gas. In some circumstances, surfaces such as those coated or impregnated with silver, platinum, enzymes, activated charcoal, or Triclosan can be used.

As shown in FIG. 2, a thermal device 71 can be in thermal connection with the container 52. Thermal device 71 can, for example, be a thermoelectric heater/cooler that can maintain the drug in a frozen state and then controllably heat the drug to any of room temperature, body temperature, or another temperature at a controlled rate. Thermal device 71 is connected to control unit 69*a*, which coordinates its operation. Thermal device 71 can, for example, help maintain the drug at a reduced temperature through passive insulation or through active chilling (for example, with dry ice or with a mechanical refrigerator). Heat can be provided in many ways including, but not limited to, a resistive heater, microwaves, chemical reaction(s), material phase change(s), or hot air.

Pump 42 can provide steady consistent flow over extended periods of time (for example, over minutes) much better than a human pushing a syringe plunger. The consistent flow provided by pump 42 reduces the risk associated with operator fatigue and/or mistakes. Also, by making the connection in a protected way, and then throwing away, as a unit, fluid path 24, containers 51 and 52, enclosure 70, and other fluid path elements, there is no opening of the fluid path that could allow the biohazardous material to escape into the environment.

Saline, other flushing fluid or another non-hazardous drug can be stored in container 51. Flow is driven or caused by pump 41. The flushing fluid flows through tubing 24*b* and 24*a*, into manifold 30 and thence into patient 1. In certain gene therapy procedures, the initial flush flow rate is preferably the same as the drug flow rate and preferably begins immediately after the flow of the drug is stopped, because it is used to flush drug out of the fluid path into patient 1. The saline can also be pumped simultaneously with the drug to provide dilution of the drug if that is advantageous. Rapid alternations between saline and drug delivery can also produce a dilution effect with the fluids mixing as they traverse the remainder of the fluid path. Additionally, in situations where two or more of the possible multiple fluids are incompatible, the flushing fluid can be used to separate the incompatible fluids before delivery to the patient. For example, some X-ray contrasts are incompatible with some gene therapy drugs.

Pumps 41 and 42 can be one of many commercially available pumps. For example, a suitable pump is the CONTINUUM™ pump available from Medrad, Inc. of Indianola, Pa. The PEGASUS™ series of pumps available from Instech Laboratories, Inc. of Plymouth Meeting, Pa., can also be used in some applications. Depending upon the details of the procedure and the number of fluids to be used, multiple hazardous fluid pumps with containment chambers and/or multiple non-hazardous fluid pumps can be used.

Where fluid lines 24*b* and 24*c* come together to start segment 24*a*, it can be useful to have one or more spring-loaded one way valves or electrically controlled valves 24*d* and 24*e*, so that there is no flow or diffusion of one fluid into another fluid. A similar use of valves is, for example, found on the disposable fluid path used with the SPECTRIS® MR injectors available from Medrad, Inc. to prevent diffusion mixing of MR contrast into the flushing fluid.

With the systems of the present invention, the operator can inject and flush the gene therapy drug much more consistently and conveniently than by current hand operated procedures. The sequence, volumes, flow rates, and durations of various injections can be effected in the same manner as those currently effected by hand, or can be much more flexible, sophisticated, or complex than is possible with separate syringes and hand injections.

Another feature of the systems of the present invention that can increase ease of use and safety is waste container 55 illustrated in FIG. 2, which is connected to manifold 30 via tubing 25. Waste container 55 can, for example, be a sealed, initially collapsed bag, or a rigid or semi-rigid container with a filtered vent. When fluid lines are first connected, they can be dry (full of air.) Because it is generally bad to inject air into a patient's blood vessels, it is necessary to prime or purge the fluid lines, that is, to push fluid through the lines to remove the air. To eliminate the chance that any biohazardous material is released into the environment, first contrast syringe 10 and manifold 30 can be primed, either into waste container 55 or using the procedures currently used. Then the biohazardous drug is primed through 24*c* and just a little bit beyond into tube 24*a*. Then the flush fluid is primed through 24*b* and 24*a* all the way into waste container 55. In this manner, no biohazardous material is released during the purging process. In an alternative embodiment, the fluid path can be primed with, for example, saline prior to connecting the fluid path to container 52. Such "prepriming" is discussed in U.S. Patent Application Publication No. 2003-0004463, filed July 2004, 2002, assigned to the assignee of the present invention, the disclosure of which is incorporated herein by reference.

Dashed lines 60, 61, 62, 63, 64, 65, 66, 67, and 68 in FIG. 2 represent communication paths for information or control transmission or transfer. In the embodiment of FIG. 2, control unit 69*a* communicates with the system pumps and the patient. Control unit 69*a* also preferably includes a user interface 69*b* through which the operator can monitor, program, or control all the associated devices. User interface 69*b* allows the operator to input settings or controls, and to assess the condition and operation of the system. In one embodiment, user interface 69*b* includes a display with a touch screen as known in the computer arts. Portions of user interface 69*b* can optionally include a foot pedal, hand switch, voice recognition, voice output, keyboard, mouse, and/or an LCD display. Control unit 69*a* can, for example, include a personal computer with a keyboard, speakers, and display that serves as user interface 69*b*. Software such as LABVIEW® available from National Instruments of Austin, Tex., is, for example, capable of collecting data and creating sophisticated control strategies based upon that data and may be incorporated into control unit 69*a*.

Communication paths 60, 61, and 62 communicate with system pumps 40, 41, and 42, respectively. Communication path 63 communicates with manifold 30 so that the proper fluid path is open at the proper time. Communication paths 65 and 66 can operate valves 24*d* and 24*e* respectively, if they are controlled valves rather than spring loaded valves. Communication path 64 is shown schematically to bring heartbeat information from patient 1 to control unit 69*a*. An instrument (not shown) can be provided that acquires the signal and conditions or operates on it before outputting it to control unit 69*a*. The instrument can, for example, be an ECG monitor, a blood pressure monitor, a pulse oximeter, image segment or region of interest extractor, or other device. If control unit 69*a* incorporates, for example, a data acquisition card (available, for example, from National Instruments) with sufficient isolation, no additional instrument is necessary. In situations where the target is an organ other than the heart, the instrument can monitor some physiological parameter or imaging aspect related to that target organ. An example is monitoring respiration where the parameters of interest are respiration rate, tidal volume and end tidal volume. Other examples are peristaltic contraction of the intestines or voluntary or stimulated contraction of muscles.

There are many varieties of communication paths. For example, communication paths can be hard-wired using the presence or absence of a voltage to activate a relay, or using a standard such as RS-232. The control lines can be electrical, hydraulic, pneumatic, mechanical, or any other advantageous communications lines. Alternatively, the communication paths can be wireless using any one of many standard protocols. The communication paths can also utilize IR data transmission methods. Additionally, one type of transmission method/protocol can be used for one communication path and another type used for a different communication path.

In addition to the benefits of fluid delivery synchronization, centralized control, and common user interface, the systems of the present invention provide the ability to overcome the need for deep subselective catheter placement to avoid reflux.

In that regard, during diastole, the heart muscle is relaxing and the chambers are filling with blood. At the same time, pressurized blood is stored in the aorta and is flowing into the coronary blood vessels. During systole, the heart muscle contracts, expelling blood from the inside of the heart. During this cycle the blood in the coronary arteries undergoes a reversal in flow direction. This is termed reflux. It is not normally a problem, and is not a problem during regular angiography. Some of the contrast is simply carried back into the aorta and out into the systemic circulation.

However, for gene therapy drugs or other toxic, hazardous or strong treatments, it is desirable to have no reflux of the hazardous substance into the systemic circulation or nearby vessels. In the current gene therapy practice, reflux is avoided by placing the catheter deep into the coronary vessels. An alternative to deep placement is to synchronize the injection of the drug with the heart beat of the patient, so that the drug flow is stopped sufficiently in advance such that the reflux of blood does not bring any drug into the aorta and thence into the systemic circulation.

Figure 3:
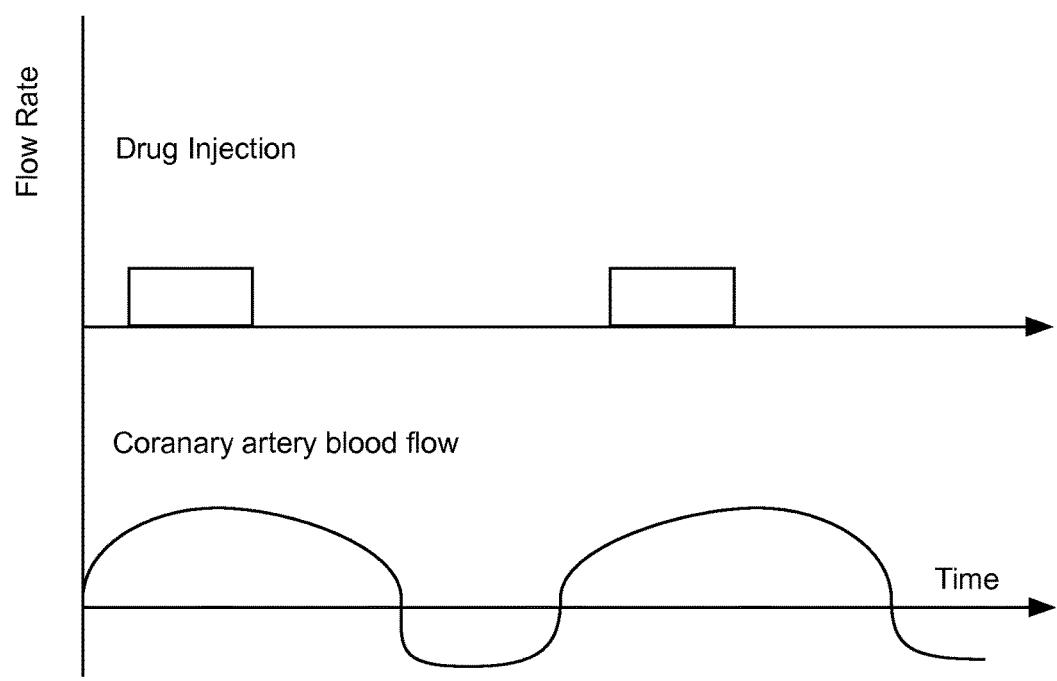
FIG. 3 illustrates a schematic diagram of pulsed injection to eliminate reflux.

FIG. 3 illustrates an example blood flow pattern and a drug injection pattern of the present invention to prevent reflux. The drug injection starts after the coronary artery flow is sufficient to carry the injection downstream and ends before the volume of blood still to pass the catheter tip is smaller than the volume of blood that is refluxed. This timing can be set with enough margin so that it operates for all patients. Alternatively, it is possible to use an imaging system with contrast test injections of various injection flow rates and/or timing (X-ray, MR, or ultrasound) and measure the amount and timing of reflux as related to a particular patient's ECG or blood pressure waveform. In addition, the catheter tip could incorporate a flow sensor that could directly measure blood flow and thus provide that information to control unit 69*a* for synchronization or for calibration and confirmation of timing in relation to the ECG and blood pressure waveform. Control unit 69*a* makes it relatively easy to inject contrast synchronized with the heart function, and by using the imaging to monitor for the presence or absence of reflux of contrast, the timing of the injection termination with respect to the heart function can be optimized.

If pump 42 cannot start and stop fast enough to deliver the necessary flow pulses, passive valve 24*e* may be replaced by an active valve that rapidly turns on and off to deliver sharp pulses. If there is too much capacitance or compliance in the fluid path from 24*e* to patient 1, then the active valve can be moved down stream to improve the bolus sharpness. The active valve can be of any suitable type including, for example electromagnetic, piezoelectric, pneumatic, or hydraulic.

In certain situations, it may be an advantage to have pump 42 or the active valve actually draw back a few microliters of fluid when the flow stops. This action draws a little blood into the catheter and thereby ensures that as blood refluxes back from the artery into the aorta, no drug can diffuse from the catheter and get into the aorta.

While the above has been described with respect to liquids in the blood vessels, and in particular the coronary arteries, similar benefits of efficient drug delivery and minimization of undesired drug migration can be achieved by synchronizing aerosol drug delivery via the lungs. The drug is provided into the air stream as air is inhaled. Drug delivery is stopped before inhalation ceases, so that all of the drug is carried deep into the lungs. Thus there is much less or no exhalation of drug.

An alternative to reflux prevention through injection synchronization is to employ occluding balloons to stop flow for a period of time while the drug is infused. The balloon inflation can be done manually or automatically. The balloon inflation device is preferably in communication with the control unit 69*a*. It can be inflated for a short period of time during which drug is delivered, then deflated, for example to allow blood to nourish the heart muscle or for another breath to be taken. This procedure can be repeated a number of times. A benefit of the occlusive approach of the present invention is that the drug is not continually being washed out of the muscle and into the venous system.

A two balloon occlusive system could be employed, with the drug injected into the space between the two balloons. This procedure allows treatment of a selected section of a blood vessel and can, for example, be useful to pretreat or post treat arterial segments that are being stented.

The fluid path of the system shown in FIG. 2 can come totally preassembled, such that the only connections needing to be made the connection to the catheter 31 and the container 52. Or, it may come as many separate pieces that are assembled by the user. If the connections are made before the hazardous pharmaceutical enters the system and are not to be subsequently opened, the connections can be simple luer lock standard connectors. For those connections that are made or possible broken and remade, such as the catheter connection, after hazardous fluid has entered the system, additional precautions should be taken. A suitable biocontainment connector will be described elsewhere.

Table 1 sets forth a brief description of the system set-up and drug delivery steps for the current practice and for the present invention and illustrates the improvements evident in a comparison of the required steps.

TABLE 1

| | |
|---|---|
| 1. Store frozen vials in the pharmacy. | a. Store frozen vials in the pharmacy |
| 2. In a pharmacy hood, using gloves and proper technique, thaw the bottle with the gene therapy drug in the hand, avoiding agitation. | b. Transport the drug bottle to the suite, install in the biohazard enclosure and thaw. (Or, install in biohazard enclosure in pharmacy and transport therein.) |
| 3. Using a needle, pull a few ml of drug into a 10 ml syringe. | |
| 4. Add a few ml of saline to dilute it. | |
| 5. Place the 10 ml syringe in a 20 ml syringe holder for transport to the interventional suite to preserve the sterility of the outside of the syringe. (Thawed drug has to be used in several hours.) | |
| 6. Operating personnel put on and wear goggles and masks with M-95 filters to protect against infection from airborne virus. | |
| 7. All the fluid lines are purged of air. The operators can dilute the drug further if there are more than 4 coronary arteries to inject. | c. Purge air from all fluid lines, ensuring that any biohazard material is delivered into the waste container 55. Connect the patient ECG to the control unit 69a. |
| 8. The catheter is positioned in the desired vessel using normal angiographic equipment and technique. Deep subselective placement can be used avoid any reflux of contrast or drug into the aorta. | d. The catheter is positioned in the desired vessel using normal angiographic equipment (manifolds, catheters, guidewires) and technique. Deep subselective placement is not needed. |
| 9. The placement is verified with a contrast injection. | e. The placement is verified with a contrast injection. |
| 10. The manifold and/or catheter are optionally | f. The operator programs the pumps to deliver the |

TABLE 1-continued

| | |
|---|---|
| flushed with saline by removing the contrast syringe and attaching the saline syringe. | proper amount with the proper timing. |
| 11. The saline syringe is disconnected, the gene therapy syringe is connected and 1 to 5 milliliters is injected by hand over 1 to 2 minutes. | |
| 12. The gene therapy syringe is disconnected and the saline syringe is connected to inject a few ml of saline over the same time period to flush the gene therapy drug out of the fluid path and into the patient. | |
| 13. The saline syringe is disconnected and the contrast syringe is reconnected to inject contrast to confirm that the catheter had not moved. | g. The drug and flush fluids are delivered as programmed. |
| 14. The catheter is then repositioned for the next injections and steps 8-12 are repeated until all vessels are injected | h. The catheter is then repositioned for the next injections and steps d-g are repeated until all vessels are injected |
| 15. The disposable parts of the system are disposed of as biohazard material. | i. The disposable parts of the system are disposed of as biohazard material. |

Communications and control in the systems of the present invention can have various levels of sophistication based upon design, verification, economic, and usability considerations. A simple level involves centralized start/stop timing or synchronization between two or more devices. A next level can, for example, be centralized programming of one or more pumps to improve operator or user convenience. A next level can, for example, involve a common programming interface for all pumps. A next level can, for example, include standard protocols involving various synchronization strategies and allowing the operator to save and recall customized protocols. The systems of the present invention provide great flexibility for designers to meet user needs.

Communications and control functions are shown schematically as coordinated by control unit 69a. However control can readily be distributed in another fashion. For example, angiographic injectors can monitor the ECG and synchronize the injection of contrast with the heart. The injector can then transmit the ECG signal or simple start-stop commands to drug pump 42 so that it can synchronize drug injection with the heart. Thus, some or all of the functions of the control unit 69a can be performed by the system pumps themselves in a distributed fashion at the convenience of the product designers or users. There need not be a specific box or piece of hardware that performs all, many or even any of the functions attributed to the control unit 69a. Control can be distributed.

In certain situations, it can be advantageous to have contrast injector or pump 40, similar to that described in U.S. patent application Ser. No. 09/982,518, filed on Oct. 18, 2001, assigned to the assignee of the present invention, the disclosure of which is incorporated herein by reference, be the primary controller, performing many of the functions of control unit 69a. In this embodiment, pumps 41 and 42 communicate to contrast pump 40 and all the operations described herein are achievable. The additional fluid delivery systems could be considered as accessories for the contrast pump 40.

To check for proper fluid line purging, air detectors such as those available from Introtech of Edgewood, N.Y., can be included at various places along the fluid path.

While the embodiments of the present invention described above include pumps that can be applied for the delivery of all the fluids related to a procedure, for either cost or historic preference, perception, or feelings of wanting to be in control, some of the pumping functions can be performed manually while others are performed mechanically. Specifically, many doctors prefer the manual "feel and control" of conducting the contrast injection. In this case only pumps 41 and 42 are used. Alternatively, mechanical delivery can be used and tactile feedback provided to the doctor to simulate the "feel and control" of manual operation. Tactile feedback is discussed in U.S. Pat. No. 5,840,026 and in U.S. patent application Ser. Nos. 09/982,518 and 10/237,139, assigned to the assignee of the present invention, the disclosures of which are incorporated herein by reference.

It is also possible to select the properties of a fluid path element, for example tubing 24a such that its volume is sufficient to hold the full volume of the drug to be delivered. In this case, the full volume of drug to be delivered in the single injection is relatively quickly injected into 24a, and then the flushing fluid is slowly infused via pump 41, pushing the drug into the patient at the desired controlled rate. Even if the volume of tubing 24a is not sufficient to hold the full volume of the drug, if the system knows the volume of fluid in the various tubings and pumps, it can operate pump 42 at an initially high rate until the drug is just about to exit the catheter, and then slow to the desired infusion rate. This saves time, and time is money.

Thus it is evident that any one, several, all, or none of the fluids can be advantageously injected by pump and the remaining can be injected by hand if the user so desires.

Figure 6:
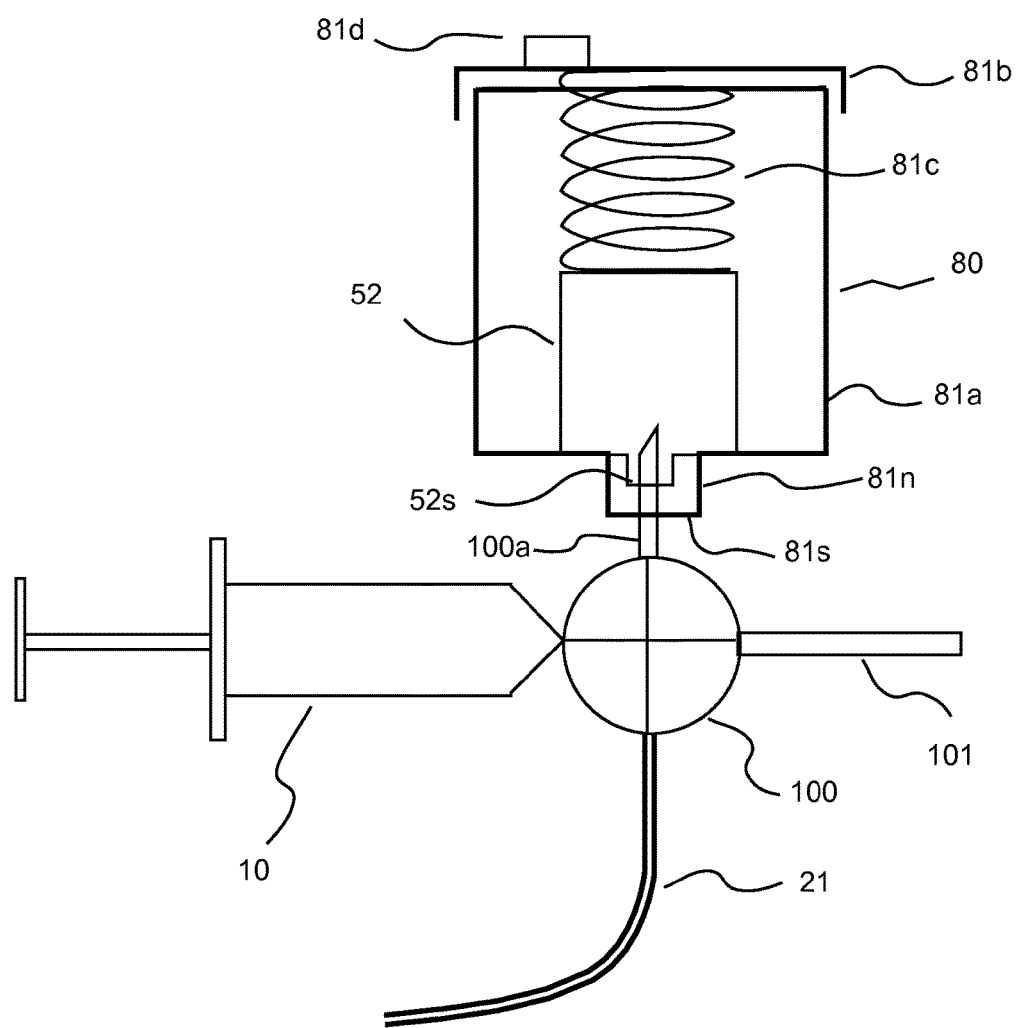
FIG. 6 illustrates a biohazard container adapted for use with a hand syringe.

If there is a reason for the doctor or operator to prefer a hand injection of the drug, then the device of FIG. 6 can be advantageous. The device of FIG. 6 incorporates the biohazard enclosure 80 or any of the various biohazard enclosures discussed herein with a multi-port valve 100 that allows manual syringe 10 to be connected to drug container 52, which is safely installed in the biohazard enclosure 80, to a source of flush fluid, saline or diluent 21, and to outlet 101, which is in fluid connection with patient 1. Outlet 101 can be a flexible tubing to connect to a catheter, or a needle for subcutaneous or intramuscular delivery of the drug. Valve 100 can, for example, include a spiked connector 100a which penetrates septum 81s of enclosure 80 and septum 52s of container 52 to place valve 100 in fluid connection with container 52. Alternatively, valve 100 can include a flexible fluid line to biohazard enclosure 80 so that biohazard enclosure 80 can be remote from the syringe 10 and valve 100. Choosing the fluid path connection by rotating the valve control lever, the operator has full manual control of the filling and delivery with the augmented safety afforded by biohazard enclosure 80 of the present invention.

Figure 7:
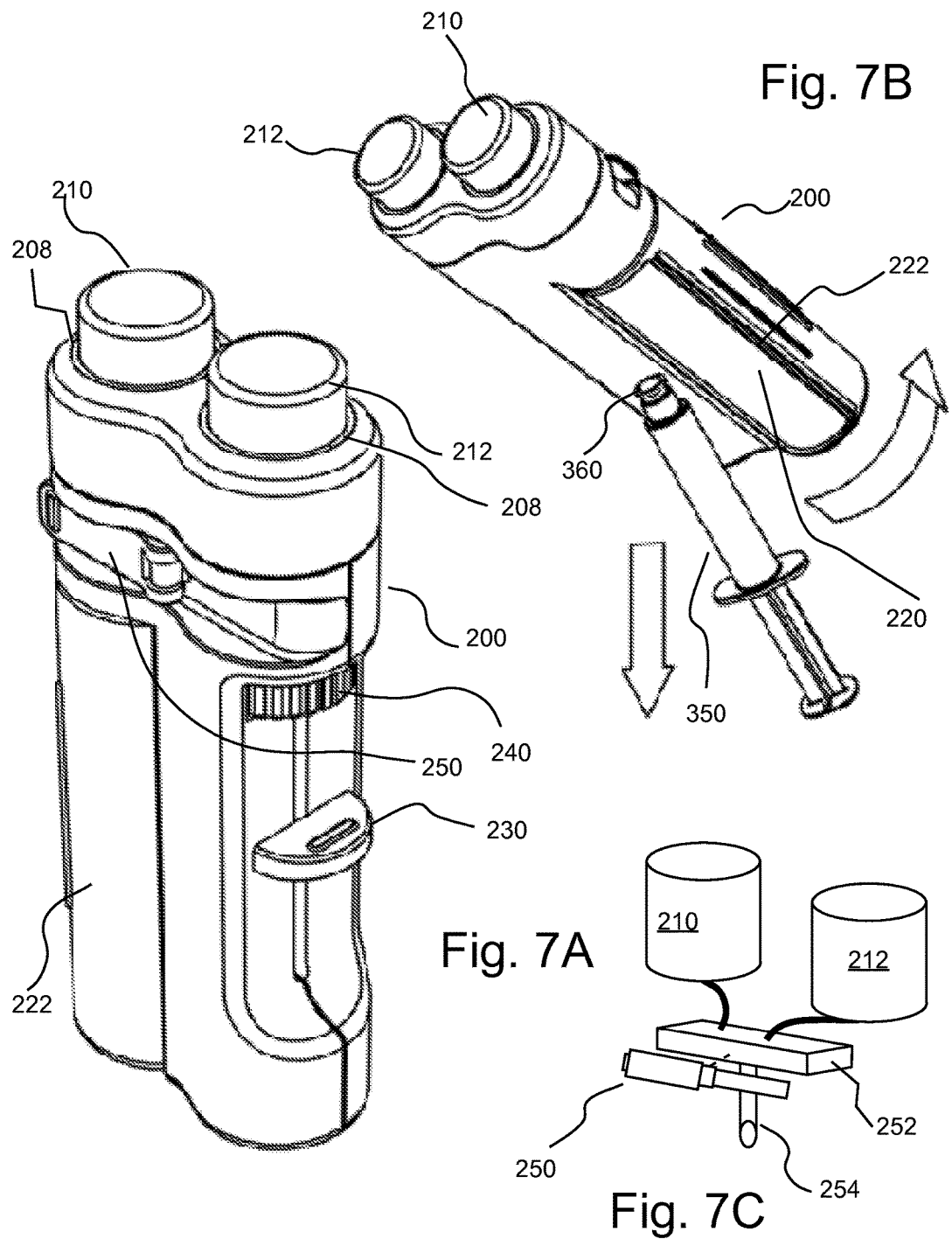
FIG. 7A illustrates a perspective view of a syringe loader including an hazardous material enclosure.
FIG. 7B illustrates another perspective of the syringe loader of FIG. 7A in which a syringe is being unloaded into the sterile field.
FIG. 7C illustrates a perspective view of one embodiment of an internal fluid path for use in the syringe loader of FIG. 7A.

FIGS. 7A through 7C illustrate another embodiment of a portion of a fluid delivery system of the present invention. Specifically this embodiment accomplishes steps 3 through 5 of table 1 without the need for a biosafety hood in a pharmacy. Loading device 200 can, for example, come preassembled with a syringe 350 inside it and can be fully sterile. A vial of saline 210 and a vial of drug 212 are inserted into openings into in the top of loading device 200. Seals 208 seal to the outside of the vials and form a biohazard enclosure. The space is vented through a filter or vent (not shown). When vials 210 and 212 are fully installed, their septums have been punctured by needles (not shown). Inside chamber shroud 222 is a syringe 350. The plunger in syringe 350 can be moved up and down by moving lever 230 for course motion or by turning thumbwheel 240 for fine motion. Lever 250 can be switched to connect the syringe first to saline vial 210 and then to drug vial 212. Syringe 350 can, for example, be in fluid connection with vial 210 and vial 212 via a spike 254, which is in sealed fluid connection with a self-sealing elastomeric plug or septum 360 (see FIG. 7C).

To fill syringe 350 with a mixture of drug and saline, the user pushes the two vials completely into device 200. Then with the lever 250 connected to saline, the user pulls in sufficient saline to purge all air from the lines into the syringe. Then the user pushes the air and some of the saline back into the saline container until the desired amount of saline remains in the syringe. The user observes the syringe through the clear shroud 222. Now the user switches lever 250, which can, for example, be in operative connection with a valve 252 (see FIG. 7C) within the housing of device 200, to the drug position and pulls fluid from drug vial 212 into syringe 350. There will be a small, consistent volume of air pulled in with the drug. The air bubble can be minimized by minimizing tubing diameter, or it can be a known consistent volume and thus be compensated for by the user. When syringe 350 is filled with the desired amount of saline and drug, the syringe can be ejected from device 200 by rotating shroud 222 and removing syringe 350. Syringe 350 can, for example, be ejected from device 200 with self-sealing elastomeric plug 360 on the end so that no drug can leak into the environment. The outside or exterior of syringe 350 can be maintained sterile so that it can be handled by sterile doctors or equipment operators. Syringe 350 could be used for hand injections, or can be connected to a pump via, for example, a system similar to that illustrated in FIG. 13 that preferably provided a containment to capture any aerosols or spills created during the making of a connection.

Figure 8:
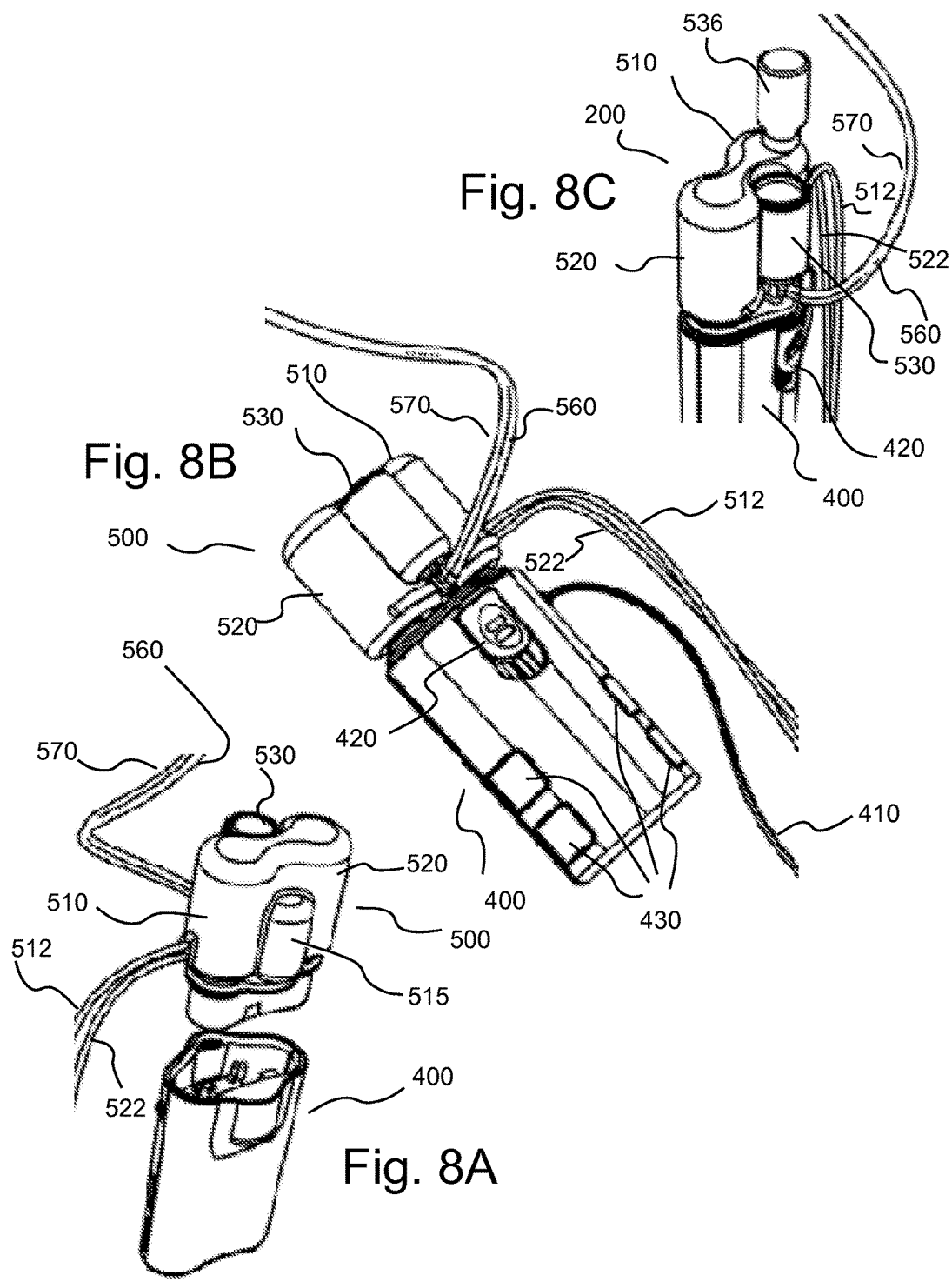
FIG. 8A illustrates one embodiment of a pump and a multi-chamber fluid container of the present invention in a disconnected state.
FIG. 8B illustrates a perspective view of the pump and a multi-chamber fluid container of FIG. 7A in a connected state.
FIG. 8C illustrates another perspective view of the pump and a multi-chamber fluid container of FIG. 7A in a connected state with the drug container ready for insertion.

FIGS. 8A through 8C illustrate another embodiment of a portion of a fluid delivery system of the present invention including an electromechanically powered injector or pump 400 which is powered by connection to a source of electrical energy via a power line 410 (see FIG. 8B). In the embodiment of FIGS. 10A through 10C a multi-chamber, multi-reservoir or multi-compartment container 500 is removably attachable to pump 400. Multi-chamber container 500 includes chambers for containment of, for example, three different fluids which can be pumped by pump 400 when multi-chamber container 500 is operably connected to pump 400 as illustrated in FIGS. 8B and 8C. A first chamber 510 can, for example, be in fluid connection with a source of saline (not shown) via tubing 512. A second chamber 520 can, for example, be in fluid connection with a source of contrast (not shown) via tubing 522. A third chamber or enclosure 530 preferably forms a hazardous material containment enclosure for use in connection with a hazardous pharmaceutical container 536 including, for example, as a gene therapy drug. Hazardous enclosure 530 can, for example, operate in a manner similar to enclosure 80 of FIG. 4 or similar to that shown in FIG. 5. Hazardous enclosure 530 can include a heating/cooling element or elements as discussed above.

Upon operation of pump 400, one or more of the fluids from chambers 510, 520 and 530 is transmitted to the patient via tubing 560 which is in fluid connection with a catheter (not shown). A second tubing line 570 can be provided to connect to a waste container 515 (similar in operation to waste container 55 of FIG. 2). Second tubing line 570 can also be used for purging air each time a connection to a catheter is broken as, for example, when switching between blood vessels for injection.

Pump 400 further includes a release latch 420 to enable disconnection of multi-chamber container 500 from pump 400. Pump 400 can further include controls 430 positioned upon the housing of pump 400 to control the operation thereof. Additionally or alternatively, a control unit remote from pump 400 can be provided. Although containers or reservoirs 510 and 520 and enclosure 530 are formed integrally in the embodiment of FIGS. 8A through 8C, one skilled in the art understands that the containers and enclosure(s) can also be separately attachable to pump 400 or a similar pump.

The system of FIGS. 8A through 8C can be used in a sterile field by encasing the reusable pump 400 in a disposable container, for example, a plastic bag, and fully contains a hazardous pharmaceutical such as a gene therapy drug. Multi-chamber container 500 can be made to be disposable. Pharmacy preparation procedures are eliminated as a result of hazardous enclosure 530. Electromechanical pump 400 provides for uniform delivery of fluid over extended periods of time with the ability to program complex flow control parameters.

Figure 9:
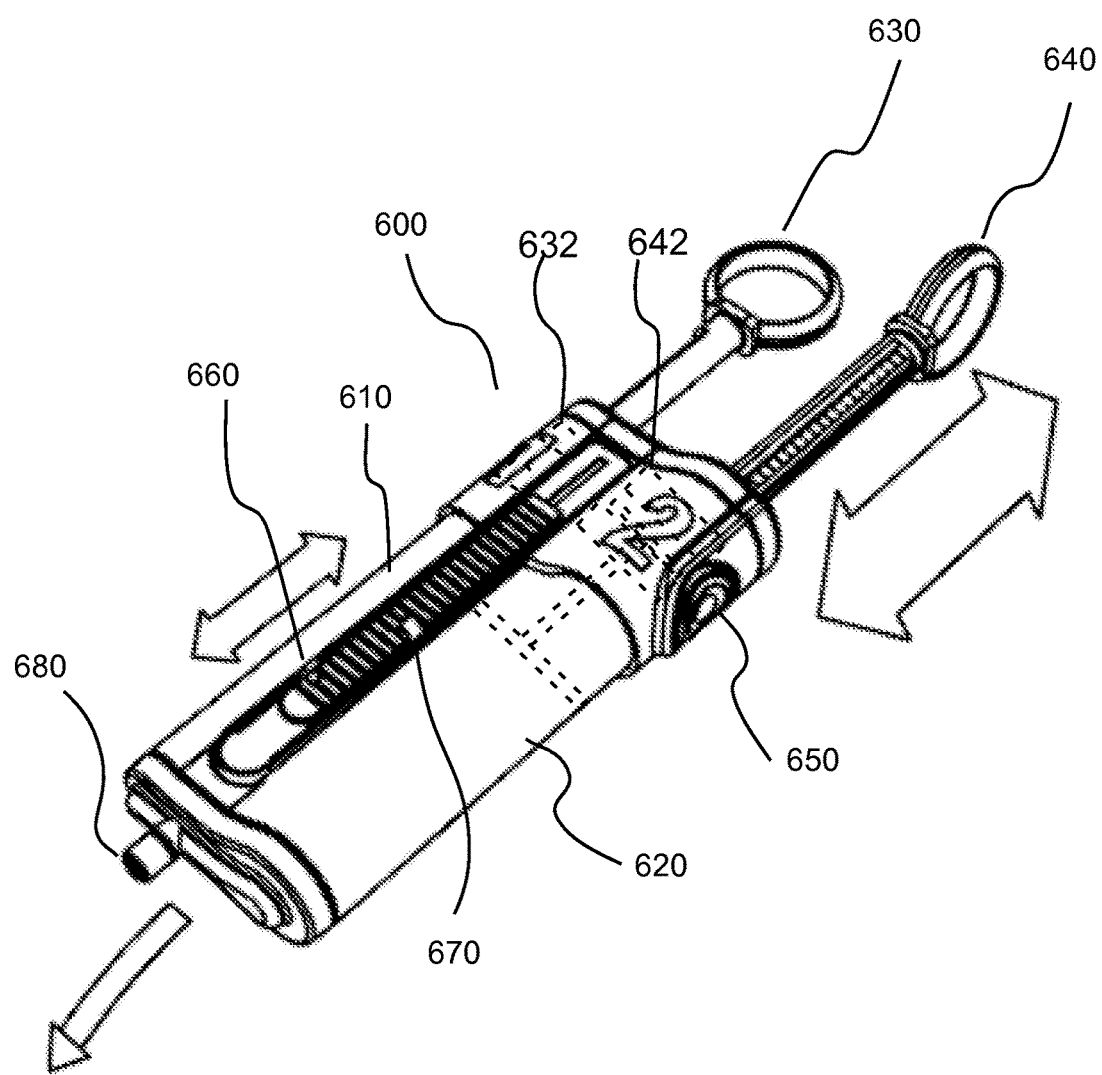
FIG. 9 illustrates an embodiment of pump mechanism of the present invention used to automate fluid delivery from multiple prepared syringes.

FIG. 9 illustrates another embodiment of the present invention in which uniform delivery of fluids over an extended period of time is automated. In this embodiment, a single disposable device 600 contains two side by side syringes, for example, a saline syringe 620 and a drug syringe 610. These can be prepared in many places, for example, in a hood in the hospital pharmacy, in the device of FIG. 7, or they preferably come preloaded with the liquids. To fill syringes 610 and 620, the operator pulls back handles 640 and 630 which also winds or bias springs 632 and 642 that store energy for pressurization of saline and drug, respectively. A control button 650 can be provided to start the flow of the drug. Adjustable stop controls 660 and 670 can be provided to control the amount of drug and saline, respectively, injected through an outlet 680 into the patient. After the selected amount of drug is delivered, the pump automatically delivers the selected amount of saline. Pump 600 can be disposable in its entirety.

FIGS. 10A through 10C illustrate a pump mechanism 700 that operates in a similar manner to pump mechanism 600. Pump 700, however, uses electromechanical power to inject fluid from disposable, front-loading syringes 800*a* and 800*b*. Pump 700 can, for example, operate in a manner similar to the dual syringe STELLANT® and SOLARIS® injector available from Medrad, Inc. Power is supplied to pump or injector 700 via power line 710.

Syringe 800*b* can include a hazardous pharmaceutical. Syringe 800*a* can, for example, be in fluid connection with a fluid path 810, which is in fluid connection with a source of another fluid (for example, saline). Preferably syringe 800b with the hazardous drug comes with fluid connections already made, or has a fluid connection such as those shown in FIGS. 13A through C such that biohazard containment is achieved.

As used herein in connection with several of the various embodiments of the present invention, the term "pump" includes all means of causing a controlled fluid flow, including controlled pumps or pressure sources and regulators, for example peristaltic pumps, gear pumps, syringe pumps, electrokinetic pumps, gravity, compressed gas, controlled gas evolving devices, spring pumps, centripetal pumps or any system which does not require continuing human exertion of motive force when the fluid is flowing. A number of the aspects of the present invention can also be advantageously applied to hand activated pumps as well.

Especially in cardiac studies, it is anticipated that more than one drug will beneficially be injected. Examples of additional drugs are cardiac stress agents, thrombolytic drugs, or drugs to decrease the chance of restenosis after angioplasty or stenting. As clear to one skilled in the art, injection of such additional substances can be accommodated by adding additional pumps, fluid reservoirs, and optionally communications lines to the systems described herein.

Non-viral gene therapy approaches can also benefit from the features of the systems of the present invention. While not as hazardous, non-viral genes still may pose hazards to healthcare workers. Minis Corp. of Madison, Wis., has, for example, published animal results in which they inject DNA not contained in a virus into the limb arteries using higher flow rates and volumes than discussed above in connection with DNA transfected via a viral vector. At high flow rates and volumes (over 100 ml), a fluid delivery system using mechanical pumps is especially beneficial.

There are also studies that discuss the injection of drugs or enzymes before injection of a gene therapy drug or other therapeutic agent. These pretreatment drugs can, for example, promote the migration or transfer of DNA from the blood vessel into the tissue. An example of such a pretreatment drug is an enzyme that breaks down collagen to make the blood vessels more porous to the gene's DNA. The systems of the present invention can be used to inject such pretreatment drugs.

The fluid delivery system of the present invention can also be used to deliver gene therapy drugs for direct injection into the heart or other tissue. In *The Scientist,* 12[10]:4 May 11, 1998, for example, a treatment is disclosed involving the direct injection of a gene therapy drug into heart muscle during open-heart surgery using 14 separate insulin (low volume) syringes and needles. The systems of the invention can eliminate the labor, cost, and risk of filling all those syringes by allowing the operator to inject multiple times directly from a common reservoir. Instead of delivering fluid to catheter 31 in such a procedure, it can be delivered via a tube to a small needle that is inserted appropriately into the heart muscle (myocardium). This also provides the safety enhancement of always flushing the line with saline after the drug, so that when a connection is opened, it is saline flush that has the potential for spillage or aerosolization, rather than the hazardous drug. In a situation such as this, it is beneficial if the user interface tells the user when the injection has been completed, and the hazardous drug has been flushed from the line so that the connection can be opened or the needle removed.

The fluid delivery system of this invention can also be used to deliver the fluid in connection with other gene uptake augmentation schemes, for example sonoporation, electroporation, or optically activated drug delivery strategies.

The fluid delivery systems, devices and methods of the present invention have been generally described above using representative examples of injection of gene therapy drugs or agents. However, the systems, devices and methods of the present invention are not limited to gene therapy applications. The systems, devices and methods of the present invention can be used in many other drug delivery and therapeutic procedures. In general, the systems, devices and methods of the present invention are particularly suited for use in connection with any hazardous pharmaceutical or substance to be injected into a patient (human or animal). As used herein, the term "pharmaceutical" refers to any substance or drug to be injected or otherwise delivered into the body (either human or animal) in a medical procedure and includes, but is not limited to, substances used in imaging procedures (for example, contrast media), diagnostic, and therapeutic substances. As described above in connection with gene therapy agents, a number of such pharmaceutical substances pose a danger to both the patient and to the personnel administering the substance if not handled and/or injected properly. Examples of hazardous pharmaceuticals include, but are not limited to, radiopharmaceuticals, biological pharmaceuticals, proteins, cells (for example stem cells or myogenic cells), chemotherapeutic pharmaceuticals and gene therapeutic pharmaceuticals. Exemplary methods of administering hazardous pharmaceuticals include intraarterial, intravenously, intramuscularly, subcutaneously, by respiration into the lungs, and transdermally. Even pharmaceuticals that are not considered to be extremely hazardous can be beneficially administered via this system and provide hospital personnel additional protection against adverse effects.

The systems of the present invention can, for example, be applied to radiotherapy drugs or pharmaceuticals wherein the drug or pharmaceutical itself is radioactive. As clear to one skilled in the art, maintaining complete containment of radiotherapy pharmaceuticals promotes safety. If the drug or pharmaceutical is radioactive, the use of radiation absorbing or leaded Plexiglas shielding will help protect the operator and patient from unnecessary radiation dose. Designers skilled in the art of radiation shielding can readily specify the thicknesses needed. Containment of radiotherapy pharmaceutical is discussed in U.S. Patent Application Publication No. 2003-0004463.

When used in connection with thrombolytic pharmaceuticals, the systems of the present invention provide, for example, the benefit of integrated control and the ability to inject the thrombolytic pharmaceutical, to inject saline, and to periodically inject contrast to verify continued correct placement of the catheter.

Likewise, the systems of the present invention can be advantageously applied to tumor and other chemotherapy in which the chemotherapy pharmaceutical is supplied to the vessels supplying a tumor or other region of interest. In the case of chemotherapy pharmaceuticals, the fluid volumes can be quite small and an occlusion balloon can be beneficial to slow or prevent the wash out of the chemotherapy from, for example, tumor tissue.

The pharmaceuticals or drugs mentioned above, or other pharmaceuticals or drugs can be included in or associated with ultrasound bubbles. The system of the present invention can deliver the bubbles to the region of interest and then ultrasound energy can be used to destroy the bubbles and promote the delivery of the drug to the tissue. The uses of ultrasound bubbles to deliver and release a pharmaceutical to a region of interest is disclosed in U.S. Pat. No. 6,397,098, assigned to the assignee of the present invention, the disclosure of which is incorporated herein by reference.

The procedure of this invention has generally been described with liquid drugs, and can also apply to powdered drugs with either a liquid or gaseous vehicle, or gaseous drugs that are to be delivered to a recipient.

Figure 11A:
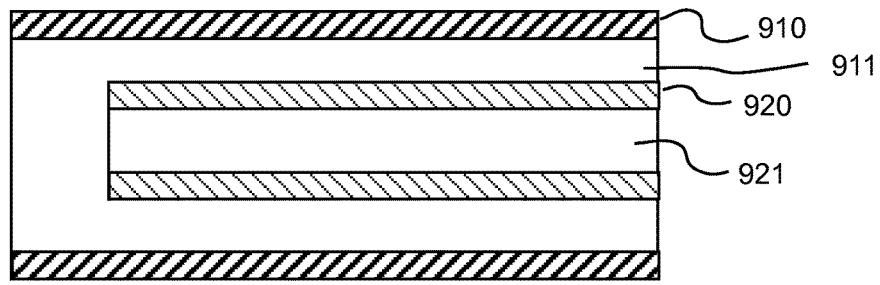
FIG. 11A illustrates a side, cross-sectional view of the end portion of an embodiment of a generally concentric, dual lumen catheter.
Figure 11B:
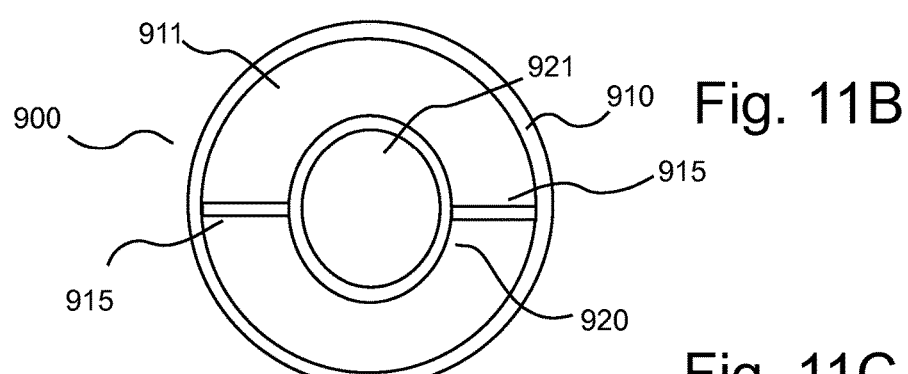
FIG. 11B illustrates an end view of the catheter of FIG. 11A.
Figure 11C:
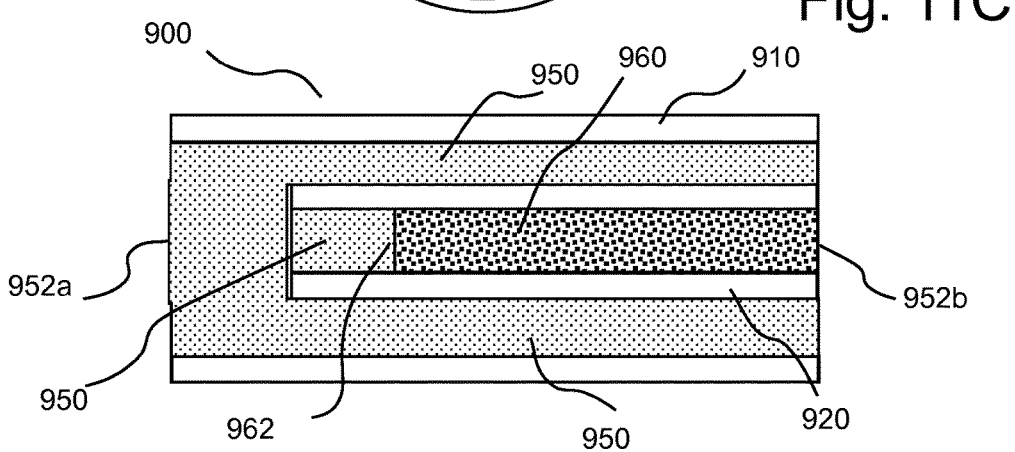
FIG. 11C illustrates a side, cut away view of the catheter of FIG. 11A with saline and a bolus of a hazardous pharmaceutical flowing therethrough.

A number of the hazardous pharmaceuticals for use in connection with the systems, devices and methods of the present invention can cause significant damage to the vessels into which they are injected. Certain antitumor chemotherapy pharmaceuticals, for example, are known to cause vessel damage when delivered through a peripheral venous catheter. FIGS. 11A through 11C illustrate an embodiment of an end portion of a dual, generally concentric lumen catheter 900 of the present invention that can be used to reduce vessel damage. In that regard, a first, outer tube or conduit 910 is provided. A second, inner tube or conduit 920 is provided within first tube 910 held by members 915 so that an outer lumen for passage of fluid and an inner lumen for passage of fluid are created. A fluid that does not cause vessel damage such as saline 950 is preferably passed through the outer lumen. Hazardous pharmaceutical 960 is preferably passed through the inner lumen.

FIG. 11C illustrates the fluid in the catheter 900. For an injection, saline starts flowing through lumen 911. No drug flows through lumen 921. After a predetermined time, drug flows through 921 and saline flow optionally is reduced by the same flow rate, so that the flow rate of fluid exiting the catheter remains constant. These flow transitions are preferably not instantaneous. When sufficient drug has been injected, then the flow of drug is reduced to 0 and the flow of saline is increased to compensate for it. After a small amount of time, the flow of drug is reversed to pull a little saline into lumen 921, as show in FIG. 11C. Then the flow of saline is stopped or reduced. In this one cycle, the full dose of pharmaceutical 960 can be delivered, or the dose can be delivered over a number of these cycles. This specific flow profile is given as an example of many flow profiles that can change over time.

Figure 11D:
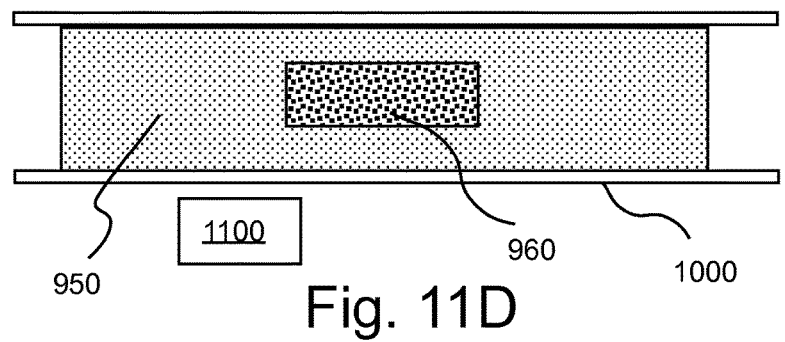
FIG. 11D illustrates the resultant flow profile through a patient vessel.

FIG. 11D illustrates the resultant flow profile within a vessel 1000. As illustrated in FIG. 11D, vessel 1000 is protected from contact with hazardous pharmaceutical 960 in the vicinity of the catheter tip by an encompassing boundary of saline. As the fluid travels down the path of vessel 1000, diluted hazardous pharmaceutical 960 may contact vessel 1000 some point, although by selecting the viscosity of the drug 960 it is possible that the bolus travels relatively undisturbed to, for example, the heart.

This flow sequence of saline and drug delivery can be continuous, until all the drug is delivered, or if desired, it can be repeated over time to spread out the drug delivery and give the patient's system an opportunity to accommodate itself to the drug, minimizing the side effects. This periodic pulsed delivery has several other advantages. For example, it is easier for an extravasation detection system to operate. Extravasation detector 1100 (represented schematically in FIG. 11D) needs only to monitor for extravasation during the brief injection time and thus is less susceptible to base line drifts that plague continuous infusion extravasation detection schemes. Extravasation detectors suitable for use in connection with the present invention are disclosed, for example, in U.S. Patent Application Publication Nos. 2003-0036674 and 2003-0036713, assigned to the assignee of the present invention, the disclosures of which are incorporated herein by reference. Another benefit is that the initial several milliliters can be saline, so that if an extravasation is detected, and the injection is stopped, no hazardous drug has been injected into the patient's tissues.

The systems, devices and methods of the present invention have been described generally in connection with treatment of a human. However, the systems, devices and methods of the present invention can also be used to treat any animal or living system in which it is desirable to provide the benefits of convenience, consistency, and safety to the application of hazardous (for example, biohazardous or chemically hazardous) pharmaceuticals.

Figure 12:
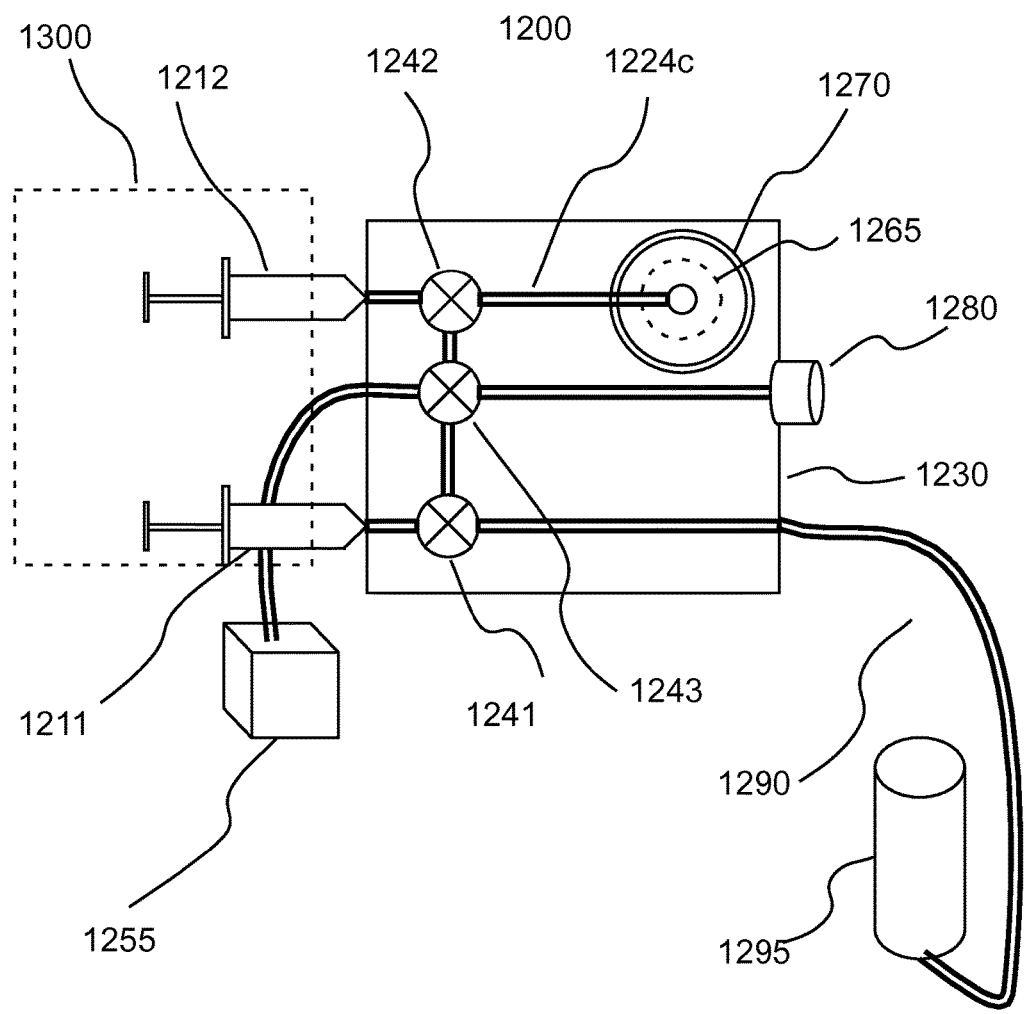
FIG. 12 illustrates an additional embodiment of the present invention.

An additional embodiment of the present invention is shown in FIG. 12. Module 1200 of FIG. 12 is, for example, disposable and manually operated. The components are a part of or connected to a base plate 1230 that incorporates fluid channels, such as 1224c. The hazardous drug container 1265 is inserted into biohazard enclosure 1270 creating a seal such that any aerosols created are contained within the enclosure. Container 1265 can, for example, be punctured or otherwise opened so that fluid can flow into fluid conduit 1224c. By pulling back on the plunger of syringe 1212, the drug is pulled through fluid conduit 1224c and valve 1242 into syringe 1212. A saline container 1295 is connected through tubing 1290. Syringe 1211 is filled with saline. Because the whole assembly is preferably small, sterile, and light, it can be easily tilted up and down for bubble removal. To fill the remaining fluid lines with liquid, valves 1242 and 1243 are turned so that syringe 1212 communicates with waste container 1255. Air can then be ejected from syringe 1212 and the intervening fluid path into waste container 1255. To avoid wasting the hazardous drug, syringe 1212 can be moved forward just enough to move the meniscus of the hazardous drug just past valve 1243 toward waste container 1255. Then valve 1241 and valve 1243 are turned so that saline syringe 1211 communicates with waste container 1255. The assembly is tilted so that any air in syringe 1211 moves out and into waste container 1255 as syringe 1211 is pushed forward. This will fill the remainder of the fluid path to the waste container with liquid. Then valve 1243 is turned so that syringe 1211 communicates with outlet 1280. Syringe 1211 is moved forward and saline is pushed to connector 1280 to remove all the air before connection to the patient.

By turning valve 1243 and operating syringes 1212 and 1211, hazardous drug and saline can be injected in sequence, as directed by the operator. While this embodiment does not have all the automatic features and safeguards of some of the other embodiments, it has the benefits of being totally disposable and having an initial lower cost than some of the devices that have reusable system components. Because syringe 1212 can be refilled in a safe manner from the drug container in the enclosure 1270, syringe 1212 can have a smaller volume and thus have a smaller diameter, which makes hand injections more accurate.

Alternatively, the module 1200 can be adapted to fit onto a reusable motive device 1300, which could for example move the two syringe pistons and turn the valves so that operation is automated. For example, the module 1200 could be attached to the front of a device similar in operation to device 700 illustrated in FIG. 10A. The module 1200 could be supported through the syringes or alternatively an additional mounting bracket (not shown) could be incorporated onto device 1300. The mounting bracket could also hold solenoids, motors, or other actuators to automatically activate valves 1241, 1242, and/or 1243. Thus the operation can be fully automatic and have the built-in safeguards described elsewhere herein. A significant benefit of this embodiment of FIG. 12 is the option of making a single disposable module 1200 that can be used by hand when, for example, a hospital cannot afford a reusable motive device, and can be mated with a reusable motive device when required or desired.

FIGS. 13A through 13D set forth several embodiments of connectors for joining two fluid path segments that include elements to contain spillage and aerosols created during making and optionally breaking of fluid path connections. The embodiments of FIGS. 13A through 13D set forth connectors that provide a modification or an improvement of the connectors set forth in U.S. Pat. No. 6,440,107 B1, assigned to the assignee of the present invention, the disclosure of which is incorporated herein by reference.

The connectors of FIGS. 13A through 13D have a number of elements in common and such like elements are number commonly. Aseptic connectors 1450a, 1450b and 1450c include a first or female member 1455 and a second or male member 1475. First member 1455 is generally cylindrical in shape and comprises a septum 1460 enclosing one end thereof. First member 1455 also includes an extending member 1462 to which a conduit or connector (not shown) such as flexible tubing or a luer connector can be attached. Extending member 1462 has a passage 1464 formed therein which is in fluid connection with an interior 1466 of first member 1455. First member 1455 also preferably comprises threading 1470 on an exterior wall thereof.

Second member 1475 includes a penetrating member 1480. Penetrating member 1480 comprises a generally cylindrical penetrating element 1482 extending from a first end thereof. A passage 1484 is formed through penetrating element 1482 and the remainder of penetrating member 1480. The second end of penetrating member 1480 forms an extending member 1486 in fluid connection with passage 1482 to which a conduit or connector (not shown) such as flexible tubing or a luer connection can be attached.

Second member 1480 also includes a swivel member 1490 rotatably connected to penetrating member 1480 as described above. Swivel member 1490 further includes threading 1492 on an interior surface thereof to cooperate with threading 1470 on first member 1455. Second member 1475 also includes opposing wing elements 1494 extending radially outward therefrom to facilitate rotation of second member 1475 relative to first member 1455 to form a threaded connection of first member 1455 and second member 1475.

Figure 13C:
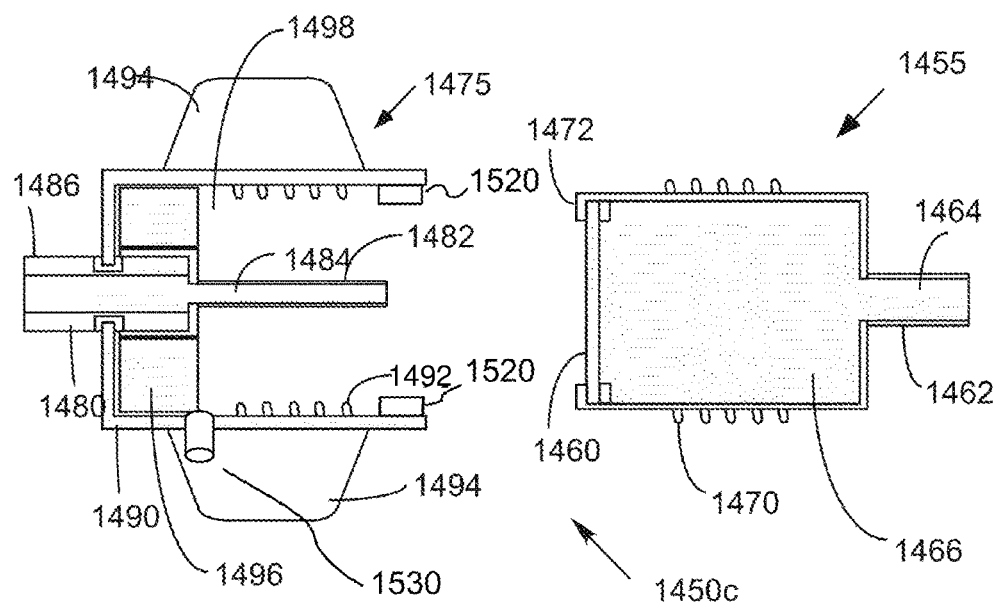
Figure 13D:
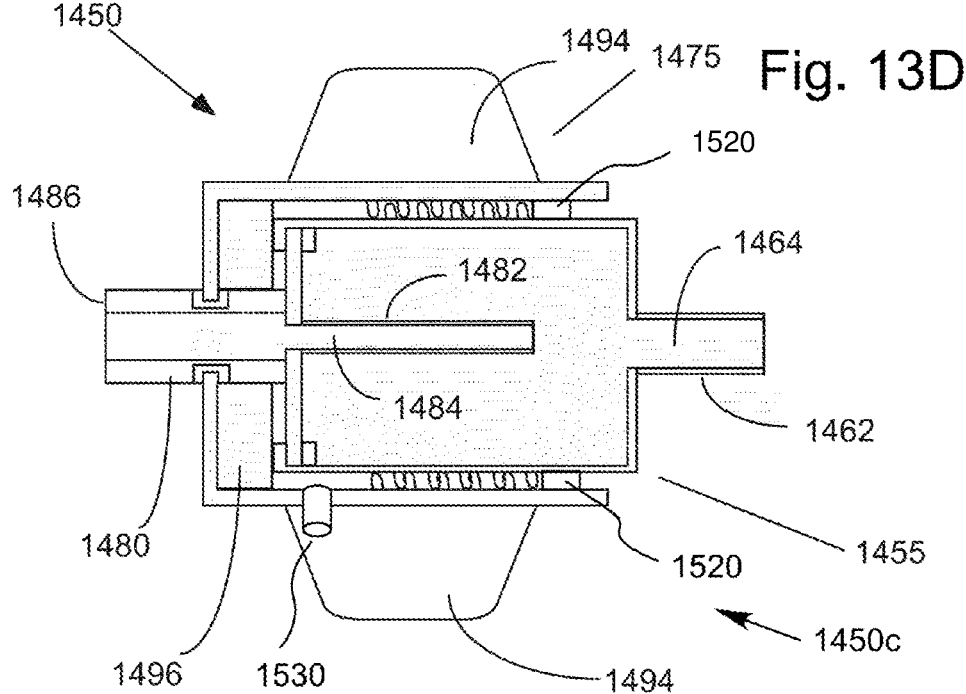

The cooperation of first member 4155 and second member 1475 to form an aseptic connection is illustrated, for example, in FIG. 13D. First member 155 and second member 1475 are first drawn axially together. As penetrating element 1482 pierces flexible septum 1460, swivel member 1490 is rotated relative to first member 1455 to engage threaded portions 1470 and 1492. As threaded portions 1470 and 1492 are tightened, bringing first member 1450 and second member 1475 in closer contact, a forward surface 1472 of first member 1455 contacts an annular, elastomeric member 1496 seated in a generally cylindrical interior chamber 1498 of second member 1475. Annular, elastomeric member 1496 is thereby compresses generally symmetrically around penetrating member 1480 and against the inner wall of swivel member 1490 to create a tight and substantially leak-proof seal between penetrating member 1480 and the interior wall of swivel member 1490. As discussed above, the substantial axial and radial forces upon annular, elastomeric member 1496 (and the resultant seal) enable use of aseptic connector 1450 at relatively high pressures.

As the connector of U.S. Pat. No. 6,440,107 B1 is assembled, the air and thence aerosols or spillage in the space 1500 (see FIG. 13A) is expelled from between the fluid path elements. The threads 1470 and 1492 provide a force but are not designed to seal air within the connector. Moreover, if threads 1470 and 1492 did seal air, then air pressure would build up as the connector was assembled.

In the embodiment of FIG. 13A, circumferential elastomeric or flexible sealing elements 1510 are attached to female connector 1455. In addition, elastomeric member 1496 is sized so that it seals the gap between penetrating member 1480 and swivel member 1490. When sealing elements 1510 contact male connector 1475, they form a seal to that connector's inner surface. The seal is maintained as threads 1492 are traversed. Alternatively as shown in FIG. 13B, sealing surfaces 1520 can be located on the inside of male connector 1475. To allow the air trapped between the two connectors to escape, the embodiment of FIGS. 13C and 13D includes a gas vent 1530. Vent 1530 preferably incorporates a micro porous filter or plug which allows air to escape but traps aerosols and spillage. Either hydrophilic or hydrophobic materials will provide some containment of aerosols. For example GORETEX®, TYVEK®, and fused polyethylene plugs are commonly used for this purpose. Activated charcoal can be incorporated in vent 1530 so that both the vapor phase and aerosols or spillage of various types of drugs are retained.

The sealing members could be incorporated into the threads themselves, by being elastomeric so that a tight fit is achieved or hollow so that they can flex sufficiently. In addition, instead of many full rotations as shown in FIGS. 13A, 13B, and 13C, a multiple threaded with only ¼ turn could be used to achieve the tightening effect and make it easier for the sealing to be achieved.

An alternative to incorporating a vent is to arrange for the air to enter the fluid path as the connector is brought together. Another alternative is to have sealing elements 1510 or 1520 incorporate open celled foam or other micro porous material such as Tyvek®, preferably incorporating activated charcoal as well, so that the air can vent through or at the seal, but drug material cannot escape.

Because positioning the angiographic catheter 31 of FIG. 2 requires that a connection be opened with the potential for release of the hazardous drug, it is advantageous if the connector of FIG. 13 be used, with the make connector 1455 with a septum being connected on the fluid source side of the fluid path and connector 1475 without a septum being an integral part of the catheter.

Although the present invention has been described in detail in connection with the above embodiments and/or examples, it should be understood that such detail is illustrative and not restrictive, and that those skilled in the art can make variations without departing from the invention. The scope of the invention is indicated by the following claims rather than by the foregoing description. All changes and variations that come within the meaning and range of equivalency of the claims are to be embraced within their scope.

What is claimed is:
1. A catheter, comprising:
an outer conduit; and
an inner conduit positioned within the outer conduit and having a diameter smaller than a diameter of the outer conduit,
wherein a volume between the outer conduit and the inner conduit define a first lumen adapted to deliver a first fluid to a patient, and an inside diameter of the inner conduit define a second lumen adapted to deliver a second fluid to the patient such that a fluid flow of the first fluid and the second fluid exiting the catheter has a flow profile where the first fluid surrounds the second fluid and the second fluid is prevented from contact with inner walls of a blood vessel of the patient in a vicinity of a tip of the catheter, wherein the first fluid is saline and the second fluid is a hazardous pharmaceutical.

2. The catheter of claim 1, wherein the inner conduit ends rearward of the outer conduit.

3. The catheter of claim 1, wherein the second fluid is an antitumor chemotherapy pharmaceutical.

4. A method for delivering a hazardous pharmaceutical comprising:

providing a catheter comprising an outer conduit, and an inner conduit positioned within the outer conduit and having a diameter smaller than a diameter of the outer conduit, wherein a volume between the outer conduit and the inner conduit define a first lumen adapted to deliver a first fluid to a patient, and an inside diameter of the inner conduit define a second lumen adapted to deliver a second fluid to the patient;

flowing the first fluid through the first lumen; and after a predetermined time, flowing the second fluid through the second lumen, wherein the fluid flow of the first fluid and the second fluid exiting the catheter has a flow profile where the first fluid surrounds the second fluid such that the second fluid is prevented from contact with inner walls of a blood vessel of the patient in a vicinity of a tip of the catheter.

5. The method of claim 4, wherein the first fluid is saline and the second fluid is a hazardous pharmaceutical.

6. The method of claim 4, further comprising reducing a flow rate of the first fluid by an amount equal to a flow rate of the second fluid at the predetermined time, such that a flow rate of the fluid exiting the catheter remains constant.

7. The method of claim 6, further comprising reducing the flow rate of the second fluid to zero after sufficient amount of the second fluid has been administered; and increasing the flow rate of the first fluid so that the flow rate of the fluid exiting the catheter remains constant.

8. The method of claim 4, wherein delivery of the second fluid is continuous until all of the second fluid is delivered.

9. The method of claim 4, wherein delivery of the second fluid is periodic and separated by delivery of only the first fluid between pulses of the second fluid.

* * * * *

UNITED STATES PATENT AND TRADEMARK OFFICE
CERTIFICATE OF CORRECTION

| | | |
|---|---|---|
| PATENT NO. | : 9,561,344 B2 | Page 1 of 1 |
| APPLICATION NO. | : 14/684900 | |
| DATED | : February 7, 2017 | |
| INVENTOR(S) | : Uber et al. | |

It is certified that error appears in the above-identified patent and that said Letters Patent is hereby corrected as shown below:

In the Specification
In Column 5, Line 23, delete "bather" and insert -- barrier --, therefor.
In Column 13, Line 53, delete "July 2004, 2002," and insert -- July 24, 2002, --, therefor.
In Column 17, Line 61, delete "Introtech" and insert -- Introtek --, therefor.
In Column 25, Lines 32-33, delete "passage 1482" and insert -- passage 1484 --, therefor.
In Column 25, Line 35, delete "Second member 1480" and insert -- Second member 1475 --, therefor.
In Column 25, Line 45, delete "first member 4155" and insert -- first member 1455 --, therefor.
In Column 25, Line 47, delete "First member 155" and insert -- First member 1455 --, therefor.
In Column 25, Line 52, delete "first member 1450" and insert -- first member 1455 --, therefor.
In Column 26, Line 8, delete "femal connector 1455" and insert -- female member 1455 --, therefor.
In Column 26, Line 11, delete "male connector 1475" and insert -- male member 1475 --, therefor.
In Column 26, Line 15, delete "male connector 1475" and insert -- male member 1475 --, therefor.
In Column 26, Line 43, delete "make connector" and insert -- female connector --, therefor.

Signed and Sealed this
Fifth Day of September, 2017

Joseph Matal
*Performing the Functions and Duties of the*
*Under Secretary of Commerce for Intellectual Property and*
*Director of the United States Patent and Trademark Office*